(12) United States Patent
Utashima

(10) Patent No.: US 11,072,809 B2
(45) Date of Patent: *Jul. 27, 2021

(54) FAD-DEPENDENT GLUCOSE DEHYDROGENASE

(71) Applicant: TOYOBO CO., LTD., Osaka (JP)

(72) Inventor: Yuu Utashima, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 395 days.

This patent is subject to a terminal disclaimer.

(21) Appl. No.: 15/650,528

(22) Filed: Jul. 14, 2017

(65) Prior Publication Data

US 2018/0030498 A1 Feb. 1, 2018

Related U.S. Application Data

(63) Continuation of application No. PCT/JP2016/050913, filed on Jan. 14, 2016.

(30) Foreign Application Priority Data

Jan. 16, 2015 (JP) .............................. JP2015-006383

(51) Int. Cl.
- *C12N 9/04* (2006.01)
- *C12Q 1/00* (2006.01)
- *C12Q 1/32* (2006.01)
- *G01N 27/327* (2006.01)

(52) U.S. Cl.
CPC ........... *C12Q 1/006* (2013.01); *C12N 9/0006* (2013.01); *C12Q 1/32* (2013.01); *C12Y 101/9901* (2013.01); *G01N 27/3271* (2013.01)

(58) Field of Classification Search
CPC .......... A61K 38/443; C12Y 101/01047; C12Y 101/006; C12N 9/0006
See application file for complete search history.

(56) References Cited

U.S. PATENT DOCUMENTS

| | | | |
|---|---|---|---|
| 7,067,295 B1 | 6/2006 | Sode | |
| 7,494,494 B2 | 2/2009 | Stoianovici et al. | |
| 7,514,250 B2 | 4/2009 | Omura et al. | |
| 7,662,600 B2 | 2/2010 | Kawaminami et al. | |
| 8,039,248 B2 * | 10/2011 | Kawaminami | C12N 9/0006 435/14 |
| 8,445,246 B2 | 5/2013 | Tajima et al. | |
| 8,492,130 B2 * | 7/2013 | Yada | C12Q 1/32 435/188 |
| 8,691,547 B2 | 4/2014 | Omura et al. | |
| 8,945,359 B2 | 2/2015 | Honda et al. | |
| 9,260,699 B2 | 2/2016 | Sumida et al. | |
| 9,404,144 B2 | 8/2016 | Sumida et al. | |
| 9,487,758 B2 | 11/2016 | Sumida et al. | |
| 9,506,042 B2 | 11/2016 | Sumida et al. | |
| 2006/0063217 A1 | 3/2006 | Omura et al. | |
| 2008/0003628 A1 | 1/2008 | Kitabayashi et al. | |
| 2008/0014612 A1 | 1/2008 | Tsuji et al. | |
| 2008/0220460 A1 | 9/2008 | Kawaminami et al. | |
| 2009/0176262 A1 | 7/2009 | Omura et al. | |
| 2009/0317848 A1 | 12/2009 | Kawaminami et al. | |
| 2010/0297743 A1 | 11/2010 | Omura et al. | |
| 2010/0323378 A1 * | 12/2010 | Honda | C12Q 1/006 435/14 |
| 2011/0053194 A1 | 3/2011 | Yuuki et al. | |
| 2011/0318810 A1 | 12/2011 | Tajima et al. | |
| 2012/0122130 A1 | 5/2012 | Omura et al. | |
| 2012/0171708 A1 * | 7/2012 | Kawaminami | C12Q 1/54 435/14 |
| 2012/0244565 A1 | 9/2012 | Nishio et al. | |
| 2013/0168263 A1 | 7/2013 | Sode et al. | |
| 2013/0309750 A1 | 11/2013 | Tajima et al. | |
| 2014/0057331 A1 | 2/2014 | Tajima et al. | |
| 2014/0154777 A1 | 6/2014 | Sumida et al. | |
| 2014/0234533 A1 | 8/2014 | Omura et al. | |
| 2014/0287445 A1 | 9/2014 | Tajima et al. | |
| 2014/0287478 A1 | 9/2014 | Sumida et al. | |
| 2015/0031059 A1 | 1/2015 | Sumida et al. | |
| 2015/0111280 A1 | 4/2015 | Sumida et al. | |
| 2015/0267178 A1 | 9/2015 | Ozawa et al. | |

FOREIGN PATENT DOCUMENTS

| | | | |
|---|---|---|---|
| JP | 2007-289148 A | | 11/2007 |
| JP | WO2008059777 | * | 5/2008 |
| JP | 2008-237210 A | | 10/2008 |
| JP | 4292486 B2 | | 7/2009 |
| JP | 4494978 B2 | | 6/2010 |

(Continued)

OTHER PUBLICATIONS

Sequence Search results for U.S. Pat. No. 9,260,699, U.S. Pat. No. 9,404,144, U.S. Pat. No. 9,487,758, 12 pages generated Jun. 21, 2019 (Year: 2019).*

Sequence Search results for WO 2008059777, 4 pgs generated Jun. 21, 2019 (Year: 2019).*

Sequence Search results for SEQ ID 3, Gencore, Jun. 20, 2019, 87 pages (Year: 2019).*

Sequence Search results for SEQ ID 4, Gencore, Jun. 20, 2019, 88 pages (Year: 2019).*

Japanese Patent Office, International Search Report in International Search Report in International Patent Application No. PCT/JP2016/050913 (dated Apr. 12, 2016).

(Continued)

*Primary Examiner* — Thane Underdahl

(74) *Attorney, Agent, or Firm* — Leydig, Voit & Mayer, Ltd.

(57) ABSTRACT

An object of the present invention is to construct a more excellent glucose sensor, and to provide GDH more suitable for the glucose sensor. Provided is FAD-dependent glucose dehydrogenase in which the range of molecular weight distribution observed by SDS-PAGE is within 50 kDa when viewed in a molecular weight distribution in which the relative value of band intensity exceeds 60% of the maximum value.

4 Claims, 6 Drawing Sheets

Specification includes a Sequence Listing.

(56) References Cited

FOREIGN PATENT DOCUMENTS

| JP | 4648993 B2 | 3/2011 |
|---|---|---|
| JP | 2011-139677 A | 7/2011 |
| JP | 2013-090621 A | 5/2013 |
| JP | 2013-116102 A | 6/2013 |
| JP | 2013-135663 A | 7/2013 |
| JP | 2013-150590 A | 8/2013 |
| WO | WO 2004/058958 A1 | 7/2004 |
| WO | WO 2006/101239 A1 | 9/2006 |
| WO | WO 2009/069381 A1 | 6/2009 |
| WO | WO 2010/053161 A1 | 5/2010 |
| WO | WO 2010/140431 A1 | 12/2010 |
| WO | WO 2011/004654 A1 | 1/2011 |
| WO | WO 2011/034108 A1 | 3/2011 |
| WO | WO 2011/068050 A1 | 6/2011 |
| WO | WO 2012/001976 A1 | 1/2012 |
| WO | WO 2012/073986 A1 | 6/2012 |
| WO | WO 2012/073987 A1 | 6/2012 |
| WO | WO 2013/022074 A1 | 2/2013 |
| WO | WO 2013/031664 A1 | 3/2013 |
| WO | WO 2013/051682 A1 | 4/2013 |
| WO | WO 2013/065623 A1 | 5/2013 |
| WO | WO 2013/118798 A1 | 8/2013 |
| WO | WO 2014/045912 A1 | 3/2014 |

OTHER PUBLICATIONS

Bak et al., "Studies on the Glucose Dehydrogenase of Aspergillus Oryzae,". *Biochim. Biophys. Acta*, 139(2): 265-276 (1967).
Bak "Studies on Glucose Dehydrogenase of Aspergillus Oryzae," *Biochim. Biophys. Acta*, 139(2): 277-293 (1967).
Bak "Studies on Glucose Dehydrogenase of Aspergillus Oryzae," *Biochim. Biophys. Acta*, 146(2): 317-327 (1967).
Bak "Studies on Glucose Dehydrogenase of Aspergillus Oryzae," *Biochim. Biophys. Acta*, 146(2): 328-335 (1967).
Chica et al., "Semi-rational approaches to engineering enzyme activity: combining the benefits of directed evolution and rational design," *Curr. Opin. Biotechnol.*, 16(4): 378-384 (2005).
Devos et al., "Practical Limits of Function Prediction," *Proteins*, 41(1): 98-107 (2000).
Guo et al., "Protein tolerance to random amino acid change," *Proc. Natl. Acad. Sci. U.S.A.*, 101(25): 9205-9210 (2004).
Hayano et al., "Purification and Properties of 3-Ketosucrose-forming Enzyme from the Cells of *Agrobacterium tumefaciens*," *J. Biol. Chem.*, 242(16): 3665-3672 (1967).
Seffernick et al., "Melamine Deaminase and Atrazine Chlorohydrolase: 98 Percent Identical but Functionally Different," *J. Bacteriol.*, 183(8): 2405-2410 (2001).
Sen et al., "Developments in Directed Evolution for Improving Enzyme Functions," *Appl. Biochem. Biotechnol.*, 143: 212-223 (2007).
Tsugawa et al., "Purification of a Marine Bacterial Glucose Dehydrogenase from Cytophaga marinoflava and its Application for Measurement of 1.5-Anhydro-D-Glucitol," *Applied Biochemistry and Biotechnology*, 56(3): 301-310 (1996).
Tsugawa et al., "Fluorescent measurement of 1,5-anhydro-D-gluctiol based on a novel marine bacterial glucose dehydrogenase," *Enzyme Microbiol. Technol.*, 22: 269-274 (1998).
Whisstock et al., "Prediction of protein function from protein sequence and structure," *Q. Rev. Biophys.*, 36(3): 307-340 (2003).
Witkowski et al., "Conversion of a β-Ketoacyl Synthase to a Malonyl Decarboxylase by Replacement of the Active-Site Cysteine with Glutamine," *Biochemistry*, 38(36): 11643-11650 (1999).
Japanese Patent Office, International Search Report in International Patent Application No. PCT/JP2012/070385 (dated Sep. 4, 2012).
Japanese Patent Office, International Search Report in International Patent Application No. PCT/JP2012/077848 (dated Jan. 15, 2013).
Japanese Patent Office, International Search Report in International Patent Application No. PCT/JP2013/052798 (dated Mar. 5, 2013).
U.S. Appl. No. 14/176,701, filed Feb. 10, 2014.
U.S. Appl. No. 14/266,304, filed Apr. 30, 2014.
U.S. Appl. No. 14/374,164, filed Jul. 23, 2014.
U.S. Appl. No. 14/584,552, filed Dec. 29, 2014.
Gan et al., "Choline Dehydrogenase [Colletotrichum gloeosporioides Nara gc5]", National Center for Biotechnology Information, Protein Database [online], GenBank Database Accession No. ELA34144 (Dec. 14, 2012).
Kisselev et al., "Polypeptide Release Factors in Prokaryotes and Eukaryotes: Same Function, Different Structure," *Structure*, 10: 8-9 (2002).
Sygmund et al., "Heterologous overexpression of *Glomerella cingulata* FAD-dependent glucose dehydrogenase in *Escherichia coil* and *Pichia pastoris*," *Microbial Cell Factories*, 10: 106 (2011).
Sygmund et al., "Reduction of quinones and phenoxy radicals by extracellular glucose dehydrogenase from *Glomerella cingulata* suggests a role in plant pathogenicity," *Microbiology*, 157(Pt. 11): 3203-3212 (2011).
Zafar et al., "Electron-transfer studies with a new flavin adenine dinucleotide dependent glucose dehydrogenase and osmium polymers of different redox potentials," *Analytical Chemistry*, 84(1): 334-341 (2012).
Japanese Patent Office, International Search Report in International Patent Application No. PCT/JP2013/067309 (dated Jul. 23, 2013).

\* cited by examiner

Fig. 1
|  | A. oryzae | A. niger | A. fumigatus | A. nidurans |
|---|---|---|---|---|
| och1 | 100% | 73% | 77% | 70% |
Fig. 2
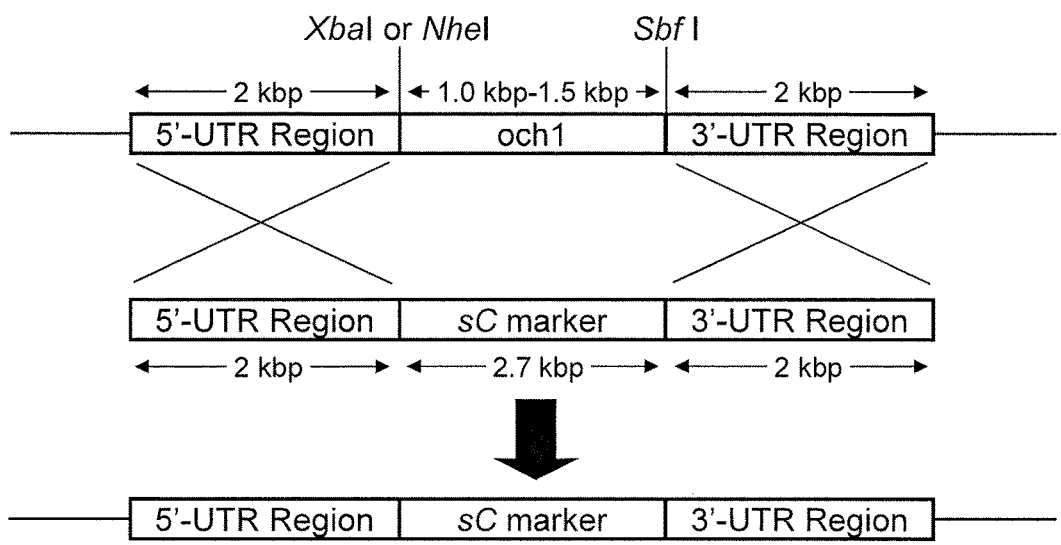
Fig. 3
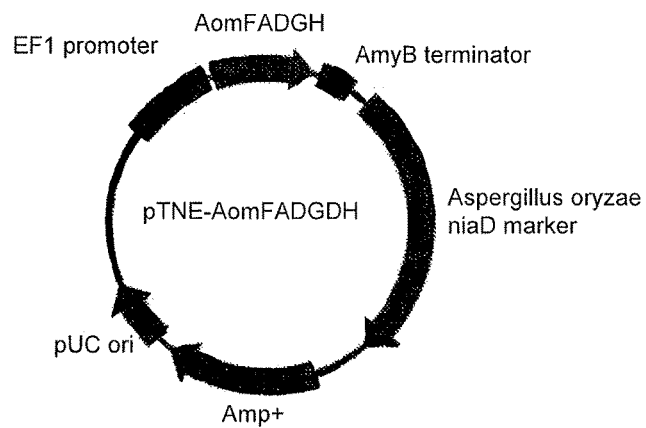

SEQUENCE LISTING

```
<160> NUMBER OF SEQ ID NOS: 24

<210> SEQ ID NO 1
<211> LENGTH: 356
<212> TYPE: PRT
<213> ORGANISM: Aspergillus oryzae

<400> SEQUENCE: 1

Met Leu Thr Tyr Arg Lys Ser Leu Ile Ala Ala Leu Phe Leu Ile Thr
1               5                   10                  15

Phe Val Val Leu Leu Arg Ser Ser His Ser Ala Ser Ser Pro Ser Pro
            20                  25                  30

Pro Ala Pro Ala His Leu Pro Asp Glu Val Ala Tyr Asn Thr Asn Glu
        35                  40                  45

Val Thr Glu Glu His Leu Ser Gly Gln Lys Lys Glu Ala Ile Pro Gln
    50                  55                  60

Gln Gln Pro Leu Lys Pro Ser Pro Ser Ala Pro Leu Arg Glu Arg Leu
65                  70                  75                  80

Arg Tyr His Phe Pro Tyr Asp Leu Asp Lys Lys Phe Pro Ala Tyr Ile
                85                  90                  95

Trp Gln Thr Trp Lys Tyr Thr Pro Asp Ser Val Trp Phe Gly Gln Glu
            100                 105                 110

Leu Arg Gly Ala Glu Ala Ser Trp Thr Glu Leu His Pro Gly Phe Val
        115                 120                 125

His Gln Val Val Pro Asp Asp Thr Gln Gly Tyr Leu Ile Lys Tyr Leu
    130                 135                 140

Tyr Ser Ser Leu Pro Asp Val Phe Glu Ala Tyr Glu Ser Leu Pro Leu
145                 150                 155                 160

Pro Val Leu Lys Ala Asp Phe Phe Arg Tyr Leu Ile Leu Leu Ala Arg
                165                 170                 175
```

Gly Gly Ile Tyr Ser Asp Ile Asp Thr Ser Ala Leu Lys Pro Ala Ala
            180                 185                 190

Asp Trp Leu Pro Ser Thr Tyr Asp Leu Ser Thr Ile Gly Phe Val Val
            195                 200                 205

Gly Ile Glu Ala Asp Pro Asp Arg Pro Asp Trp His Glu Trp Tyr Ser
210                 215                 220

Arg Arg Leu Gln Phe Cys Gln Trp Thr Ile Gln Ser Lys Pro Gly His
225                 230                 235                 240

Pro Ile Leu Arg Asp Ile Val Ala Tyr Ile Thr Glu Glu Thr Leu Arg
                245                 250                 255

Met Lys Lys Ala Gly Ile Leu Lys Val Gly Lys Met Asp Lys Thr Ile
            260                 265                 270

Val Glu Phe Thr Gly Pro Gly Ala Trp Thr Asp Ala Ile Phe Arg Tyr
            275                 280                 285

Phe Asn Asp Pro Asp Tyr Phe Asn Ile Glu Pro Asp Ser Asn His Asn
        290                 295                 300

Ile Thr Tyr Glu Asp Phe Ser Asn Gln Lys Asp Trp Arg Lys Val Gly
305                 310                 315                 320

Asp Val Val Leu Pro Ile Thr Ser Phe Ser Pro Gly Val Met Gln
                325                 330                 335

Met Gly Ala Gly Asp Tyr Asp Asp Pro Met Ala Phe Val Lys His Asp
            340                 345                 350

Phe Glu Gly Thr
        355

<210> SEQ ID NO 2
<211> LENGTH: 1071
<212> TYPE: DNA
<213> ORGANISM: Aspergillus oryzae

<400> SEQUENCE: 2
atgctcacct accgaaagtc gctcattgcg ccctcttcc tgatcacctt cgtcgtcctc      60
ctaaggtctt cccattcggc ttcctccccc tcgccccctg cgccggcaca cctcccgat    120 gaggtcgcct acaacactaa tgaagtaacg gaagagcact tgtcaggaca gaaaaaagag    180
gcgataccac agcaacagcc actcaaaccc tccccgagcg caccttgcg cgaacggtta    240 cgctaccatt tcccctacga tcttgataag aaattccccg catacatctg cagacatgg    300 aaatataccc ccgactcagt gtggttcggc aagagctgc gcggtgcgga ggcaagttgg    360
actgagctcc accccggctt cgtccaccag gtggttccag acgacaccca gggttacctc    420
atcaaatacc tatacagctc tcttcccgac gtgtttgaag cctacagtc gttgccgttg    480 cccgtcctga agccgactt cttcagatac ttgatcctgc tggcccgtgg cggaatctat    540
agcgacatcg acaccagcgc tctgaagccg gctgccgatt ggttgccctc gacctacgac    600
ctgtccacca ttggattcgt ggtcggcatc gaggcggatc ctgaccgtcc ggactggcat    660
gaatggtatt cccggagact ccaattctgt caatggacca ttcagtccaa accgggacat    720
cccatccttc gcgacatcgt ggcctacatc acggaggaaa cactacggat gaagaaggct    780
ggaatcttaa aggtcggcaa gatggataag acaatcgtgg agttcaccgg accgggcgca    840
tggacagacg ctatcttcag atatttcaac gacccagact acttcaacat cgaacccgat    900
tcaaaccaca acattaccta tgaggatttc tcgaaccaaa aagattggag aaaggtcggc    960
gacgtggtag ttctacccat tacgagcttc agccctggcg ttatgcaaat gggcgcaggc   1020
gactacgatg atccaatggc cttcgtcaag cacgacttcg aaggtaccta a    1071

<210> SEQ ID NO 3
<211> LENGTH: 572
<212> TYPE: PRT
<213> ORGANISM: Aspergillus oryzae

<400> SEQUENCE: 3

Met Lys Asn Thr Thr Tyr Asp Tyr Ile Val Val Gly Gly Thr
1               5                   10                  15

Ser Gly Leu Val Val Ala Asn Arg Leu Ser Glu Asn Pro Asp Val Ser
                20                  25                  30

Val Leu Leu Leu Glu Ala Gly Ala Ser Val Phe Asn Asn Pro Asp Val
            35                  40                  45

Thr Asn Ala Asn Gly Tyr Gly Leu Ala Phe Gly Ser Ala Ile Asp Trp
    50                  55                  60

Gln Tyr Gln Ser Ile Asn Gln Ser Tyr Ala Gly Gly Lys Gln Gln Val
65                  70                  75                  80

Leu Arg Ala Gly Lys Ala Leu Gly Gly Thr Ser Thr Ile Asn Gly Met
                85                  90                  95

Ala Tyr Thr Arg Ala Glu Asp Val Gln Ile Asp Val Trp Gln Lys Leu
            100                 105                 110

Gly Asn Glu Gly Trp Thr Trp Lys Asp Leu Leu Pro Tyr Tyr Leu Lys
        115                 120                 125

Ser Glu Asn Leu Thr Ala Pro Thr Ser Ser Gln Val Ala Ala Gly Ala
    130                 135                 140

Ala Tyr Asn Pro Ala Val Asn Gly Lys Glu Gly Pro Leu Lys Val Gly
145                 150                 155                 160

Trp Ser Gly Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
            260                 265                 270

Ile Ile Ser Ala Gly Ala Leu Arg Ser Pro Leu Ile Leu Glu Leu Ser
        275                 280                 285

Gly Val Gly Asn Pro Thr Ile Leu Lys Lys Asn Asn Ile Thr Pro Arg
    290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335

Thr Tyr Pro Ser Ile Ser Asp Val Phe Gly Asn Glu Thr Asp Ser Ile
            340                 345                 350

Val Ala Ser Leu Arg Ser Gln Leu Ser Asp Tyr Ala Ala Ala Thr Val
        355                 360                 365

```
Lys Val Ser Asn Gly His Met Lys Gln Glu Asp Leu Glu Arg Leu Tyr
    370                 375                 380

Gln Leu Gln Phe Asp Leu Ile Val Lys Asp Lys Val Pro Ile Ala Glu
385                 390                 395                 400

Ile Leu Phe His Pro Gly Gly Asn Ala Val Ser Ser Glu Phe Trp
                405                 410                 415

Gly Leu Leu Pro Phe Ala Arg Gly Asn Ile His Ile Ser Ser Asn Asp
                420                 425                 430

Pro Thr Ala Pro Ala Ala Ile Asn Pro Asn Tyr Phe Met Phe Glu Trp
            435                 440                 445

Asp Gly Lys Ser Gln Ala Gly Ile Ala Lys Tyr Ile Arg Lys Ile Leu
450                 455                 460

Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
                485                 490                 495

Leu Lys Ala Asn Tyr Arg Ser Asn Phe His Pro Val Gly Thr Ala Ala
                500                 505                 510

Met Met Pro Arg Ser Ile Gly Gly Val Val Asp Asn Arg Leu Arg Val
            515                 520                 525

Tyr Gly Thr Ser Asn Val Arg Val Val Asp Ala Ser Val Leu Pro Phe
530                 535                 540

Gln Val Cys Gly His Leu Val Ser Thr Leu Tyr Ala Val Ala Glu Arg
545                 550                 555                 560

Ala Ser Asp Leu Ile Lys Glu Asp Ala Lys Ser Ala
                565                 570
```

<210> SEQ ID NO 4
<211> LENGTH: 592
<212> TYPE: PRT
<213> ORGANISM: Aspergillus terreus

<400> SEQUENCE: 4

```
Met Leu Gly Lys Leu Ser Phe Leu Ser Ala Leu Ser Leu Ala Val Ala
1               5                   10                  15

Ala Pro Leu Ser Asn Ser Thr Ser Ala Lys Tyr Asp Tyr Ile Val Ile
                20                  25                  30

Gly Gly Gly Thr Ser Gly Leu Ala Val Ala Asn Arg Leu Ser Glu Asp
            35                  40                  45

Pro Asn Val Asn Val Leu Ile Leu Glu Ala Gly Gly Ser Val Trp Asn
50                  55                  60

Asn Pro Asn Val Thr Asn Val Asp Gly Tyr Gly Leu Ala Phe Gly Ser
65                  70                  75                  80

Asp Ile Asp Trp Gln Tyr Gln Ser Val Asn Gln Pro Tyr Gly Gly Asn
                85                  90                  95

Leu Ser Gln Val Leu Arg Ala Gly Lys Ala Leu Gly Gly Thr Ser Thr
                100                 105                 110

Ile Asn Gly Met Ala Tyr Thr Arg Ala Glu Asp Val Gln Ile Asp Ala
            115                 120                 125

Trp Glu Thr Ile Gly Asn Thr Gly Trp Thr Trp Lys Asn Leu Phe Pro
130                 135                 140

Tyr Tyr Arg Lys Ser Glu Asn Phe Thr Val Pro Thr Lys Ser Gln Thr
145                 150                 155                 160

Ser Leu Gly Ala Ser Tyr Glu Ala Gly Ala His Gly His Glu Gly Pro
                165                 170                 175
```

```
Leu Asp Val Ala Phe Thr Gln Ile Glu Ser Asn Asn Leu Thr Thr Tyr
            180                 185                 190

Leu Asn Arg Thr Phe Gln Gly Met Gly Leu Pro Trp Thr Glu Asp Val
            195                 200                 205

Asn Gly Gly Lys Met Arg Gly Phe Asn Leu Tyr Pro Ser Thr Val Asn
            210                 215                 220

Leu Glu Glu Tyr Val Arg Glu Asp Ala Ala Arg Ala Tyr Tyr Trp Pro
225                 230                 235                 240

Tyr Lys Ser Arg Pro Asn Leu His Val Leu Leu Asn Thr Phe Ala Asn
            245                 250                 255

Arg Ile Val Trp Asp Gly Glu Ala His Asp Gly His Ile Thr Ala Ser
            260                 265                 270

Gly Val Glu Ile Thr Ser Arg Asn Gly Thr Val Arg Val Ile Asn Ala
            275                 280                 285

Glu Lys Glu Val Ile Val Ser Ala Gly Ala Leu Lys Ser Pro Ala Ile
            290                 295                 300

Leu Glu Leu Ser Gly Ile Gly Asn Pro Ser Val Leu Asp Lys His Asn
305                 310                 315                 320

Ile Pro Val Lys Val Asn Leu Pro Thr Val Gly Glu Asn Leu Gln Asp
            325                 330                 335

Gln Val Asn Ser His Met Asp Ala Ser Gly Asn Thr Ser Ile Ser Gly
            340                 345                 350

Thr Lys Ala Val Ser Tyr Pro Asp Val Tyr Asp Val Phe Gly Asp Glu
            355                 360                 365

Ala Glu Ser Val Ala Lys Gln Ile Arg Ala Asn Leu Lys Gln Tyr Ala
            370                 375                 380

Ala Asp Thr Ala Lys Ala Asn Gly Asn Ile Met Lys Ala Ala Asp Leu
385                 390                 395                 400

Glu Arg Leu Phe Glu Val Gln Tyr Asp Leu Ile Phe Lys Gly Arg Val
            405                 410                 415

Pro Ile Ala Glu Val Leu Asn Tyr Pro Gly Ser Ala Thr Ser Val Phe
            420                 425                 430

Ala Glu Phe Trp Ala Leu Leu Pro Phe Ala Arg Gly Ser Val His Ile
            435                 440                 445

Gly Ser Ser Asn Pro Ala Glu Phe Pro Val Ile Asn Pro Asn Tyr Phe
            450                 455                 460

Met Leu Asp Trp Asp Ala Lys Ser Tyr Val Ala Val Ala Lys Tyr Ile
465                 470                 475                 480

Arg Arg Ser Phe Glu Ser Tyr Pro Leu Ser Ile Val Lys Glu Ser
            485                 490                 495

Thr Pro Gly Tyr Asp Val Ile Pro Arg Asn Ala Ser Glu Gln Ser Trp
            500                 505                 510

Lys Glu Trp Val Phe Asp Lys Asn Tyr Arg Ser Asn Phe His Pro Val
            515                 520                 525

Gly Thr Ala Ala Met Met Pro Arg Glu Ile Gly Gly Val Val Asp Glu
            530                 535                 540

Arg Leu Asn Val Tyr Gly Thr Thr Asn Val Arg Val Val Asp Ala Ser
545                 550                 555                 560

Val Leu Pro Phe Gln Val Cys Gly His Leu Val Ser Thr Leu Tyr Ala
            565                 570                 575

Val Ala Glu Arg Ala Ala Asp Leu Ile Lys Ala Asp Ala Gly Arg Arg
            580                 585                 590
```

<210> SEQ ID NO 5
<211> LENGTH: 641
<212> TYPE: PRT
<213> ORGANISM: Mucor prainii

<400> SEQUENCE: 5

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Thr Val Gly Gly Val Ala Gly Leu Ala Leu Ala Ser
                35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
370                 375                 380
```

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
            405                 410                 415

Asn Ser Thr Asp Glu Trp Ala Asn Tyr Tyr Ala Ser Thr Asn Ala Ser
        420                 425                 430

Asn Val Glu Leu Leu Lys Lys Gln Tyr Ala Ile Val Ala Ser Arg Tyr
    435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn

<210> SEQ ID NO 6
<211> LENGTH: 635
<212> TYPE: PRT
<213> ORGANISM: Mucor hiemalis

<400> SEQUENCE: 6

Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
            20                  25                  30

Ile Val Gly Gly Gly Val Gly Gly Leu Ala Leu Ala Ser Arg Leu Ser
        35                  40                  45

Glu Asp Lys Ser Val Thr Val Ala Val Leu Glu Ala Gly Pro Asn Ala
    50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
            100                 105                 110

```
Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
        130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
                180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
        210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
                260                 265                 270

Val Gly Val Glu Trp Tyr Thr Thr Gly Asp Asn Ser Asn Lys Gln Thr
        275                 280                 285

Ile Lys Ala Arg Arg Glu Val Ile Val Ser Ser Gly Ser Ile Gly Ser
        290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
                340                 345                 350

Gly Phe Thr Thr Asp Ser Val Phe Gln Asn Glu Thr Leu Ala Glu Glu
        355                 360                 365

Gln Arg Gln Gln Tyr Tyr Asn Asn Lys Thr Gly Ile Trp Thr Thr Thr
        370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
                420                 425                 430

Leu Leu Lys Lys Gln Tyr Ala Ile Val Ala Ser Arg Tyr Glu Glu Asn
        435                 440                 445

Tyr Leu Ser Pro Ile Glu Ile Asn Phe Thr Pro Gly Tyr Gly Gly Thr
        450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
                500                 505                 510

Asp Val Asp Val His Ile Ala Ser Thr Lys Leu Ala Arg Arg Ile Leu
        515                 520                 525
```

-continued

```
Gly Ala Glu Pro Gly Leu Ala Ser Ile Asn Ser Gly Ile Gln Pro
                530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
                580                 585                 590

Ala Asn Leu Arg Val Val Asp Ala Ser Ile Met Pro Leu Glu Ile Ser
                595                 600                 605

Ser His Leu Met Gln Pro Thr Tyr Gly Val Ala Glu Lys Ala Ala Asp
                610                 615                 620

Ile Ile Lys Met Ser Arg Lys Asn Asn Asn
625                 630                 635

<210> SEQ ID NO 7
<211> LENGTH: 633
<212> TYPE: PRT
<213> ORGANISM: Mucor subtilissimus

<400> SEQUENCE: 7

Met Arg Leu Ser Leu Ala Ile Leu Ser Leu Thr Ser Ala Leu Val Thr
1               5                   10                  15

Val Thr Ser Ala Gln Gln Asn Gly Thr Ser Asn Asp Thr Tyr Asp Tyr
                20                  25                  30

Val Ile Val Gly Gly Gly Val Gly Gly Leu Ser Leu Ala Ser Arg Leu
                35                  40                  45

Ser Glu Asp Lys Gly Val Thr Val Ala Val Leu Glu Ser Gly Pro Tyr
50                  55                  60

Ala Asp Asp Arg Phe Val Val Tyr Ala Pro Gly Met Tyr Gly Gln Ala
65                  70                  75                  80

Val Gly Thr Glu Leu Cys Pro Leu Leu Pro Thr Val Pro Gln Val Gly
                85                  90                  95

Met Asn Asn Arg Thr Ile Thr Ile Ala Thr Gly Arg Leu Leu Gly Gly
                100                 105                 110

Gly Ser Ala Val Asn Gly Leu Val Trp Thr Arg Gly Ala Met Lys Asp
                115                 120                 125

Phe Asp Ala Trp Glu Glu Leu Gly Asn Pro Gly Trp Asn Gly Lys Thr
                130                 135                 140

Met Phe Lys Tyr Phe Lys Lys Ile Glu Asn Phe His Pro Pro Thr Glu
145                 150                 155                 160

Glu Gln Val Gln Tyr Gly Ala Thr Tyr Gln Lys Asn Val His Gly Ser
                165                 170                 175

Gly Gly Pro Ile Asp Ile Ser Phe Pro Val Phe Glu Pro Gln Ser
                180                 185                 190

Ala Asn Trp Asn Ala Ser Leu Ala Tyr Leu Asn Phe Thr His Gln Gln
                195                 200                 205

Asp Leu Leu Asn Gly Ser Leu His Gly Tyr Ser Thr Thr Pro Asn Thr
                210                 215                 220

Leu Asn Pro Glu Thr Ala Arg Arg Ala Asp Ala Tyr Ala Gly Tyr Ile
225                 230                 235                 240

Gln Pro Asn Val Asn Arg Thr Asn Leu Ala Val Leu Ala Asn His Thr
                245                 250                 255

Val Ser Arg Ile Gln Phe Glu Lys Ser Asn Gly Ser Gln Pro Leu Lys
                260                 265                 270
```

Ala Ile Gly Val Glu Trp Tyr Thr Thr Gly Asp Lys Ser Thr Lys
    275                 280                 285

Gln Thr Ile Lys Ala Arg Arg Glu Val Ile Ile Ser Ser Gly Ala Ile
290                 295                 300

Gly Ser Pro Lys Leu Leu Glu Val Ser Gly Ile Gly Asn Lys Gln Ile
305                 310                 315                 320

Val Thr Ala Ala Gly Val Glu Ser Leu Ile Asp Leu Pro Gly Val Gly
                325                 330                 335

Ser Asn Met Gln Asp His Val His Ala Val Thr Val Ser Thr Thr Asn
            340                 345                 350

Ile Glu Gly Tyr Thr Thr Asn Ser Val Phe Thr Asn Glu Thr Leu Ala
        355                 360                 365

Gln Glu Gln Lys Asp Leu Tyr Tyr Asn Asn Lys Thr Gly Ile Trp Thr
    370                 375                 380

Thr Thr Pro Asn Asn Leu Gly Tyr Pro Ser Pro Ser Gln Leu Phe Thr
385                 390                 395                 400

Asn Thr Thr Phe Arg Ser Gly Lys Gln Phe Ala Ala Met Ile Arg Asn
                405                 410                 415

Ser Thr Asp Lys Tyr Ala Gln Tyr Tyr Ala Ser Thr Lys Asn Ala Thr
            420                 425                 430

Asn Ile Gln Leu Leu Lys Lys Gln Tyr Ala Ile Val Ala Arg Arg Tyr
        435                 440                 445

Glu Glu Asp Tyr Ile Ser Pro Ile Glu Ile Asn Phe Thr Pro Gly Tyr
    450                 455                 460

Gly Gly Thr Gly Glu Val Asp Leu Gln Asn Asn Lys Tyr Gln Thr Val
465                 470                 475                 480

Asn His Val Leu Val Ala Pro Leu Ser Arg Gly Tyr Thr His Ile Asn
                485                 490                 495

Ser Ser Asp Ile Glu Asp Pro Val Val Ile Asp Pro Gln Tyr Tyr Ser
            500                 505                 510

His Pro Leu Asp Val Asp Val His Val Ala Ser Thr Gln Leu Ala Arg
        515                 520                 525

Ser Ile Leu Asn Ala Pro Ala Leu Ala Ala Ile Asn Ser Gly Glu Val
    530                 535                 540

Glu Pro Gly Glu Lys Ile Gln Thr Asp Gln Asp Val Arg Lys Trp Leu
545                 550                 555                 560

Ser Asp Asn Val Arg Ser Asp Trp His Pro Val Gly Thr Cys Ala Met
                565                 570                 575

Leu Pro Lys Gly Leu Gly Val Val Asp Ser Asn Leu Lys Val Tyr
            580                 585                 590

Gly Thr Ala Asn Leu Arg Val Val Asp Ala Ser Ile Ile Pro Leu Glu
        595                 600                 605

Ile Ser Ser His Leu Met Gln Pro Val Tyr Ala Val Ser Glu Arg Ala
    610                 615                 620

Ala Asp Ile Ile Lys Gly Ser Arg Asn
625                 630

<210> SEQ ID NO 8
<211> LENGTH: 637
<212> TYPE: PRT
<213> ORGANISM: Circinella simplex

<400> SEQUENCE: 8

Met Lys Ile Ser Ala Ala Val Val Thr Ile Val Thr Ala Phe Ala Ser

-continued

```
1               5                   10                  15
Val Ala Thr Ala Gln Gln Asn Thr Ser Glu Thr Asn Thr Tyr Asp
                20                  25                  30

Tyr Val Ile Val Gly Gly Val Gly Gly Leu Ala Leu Ala Ser Arg
                35                  40                  45

Leu Ser Glu Asn Lys Gly Val Ser Ala Val Leu Glu Ala Gly Pro
                50                  55                  60

Tyr Ala Gly Asp Gln Phe Val Val Tyr Ala Pro Gly Met Tyr Gly Gln
65                  70                  75                  80

Ala Val Gly Thr Asp Leu Cys Pro Leu Leu Pro Thr Thr Pro Gln Glu
                85                  90                  95

Asn Met Gly Asn Arg Ser Leu Ser Ile Ala Thr Gly Lys Leu Leu Gly
                100                 105                 110

Gly Gly Ser Ser Val Asn Gly Leu Val Trp Thr Arg Gly Gly Leu Lys
                115                 120                 125

Asp Phe Asp Ala Trp Glu Glu Leu Gly Asn Pro Gly Trp Asn Gly Ala
                130                 135                 140

Ser Met Phe Asn Tyr Phe Lys Lys Val Glu Asn Phe Thr Pro Pro Thr
145                 150                 155                 160

Pro Ala Gln Ala Ala Tyr Gly Ala Thr Tyr Gln Lys Asn Ala His Gly
                165                 170                 175

Thr Lys Gly Pro Met Asp Val Ser Phe Thr Asn Phe Glu Phe Pro Gln
                180                 185                 190

Ser Gly Asn Trp Asn Ala Ser Leu Asn Ala Val Gly Phe Thr Ala Val
                195                 200                 205

Pro Asp Leu Leu Asn Gly Thr Leu His Gly Tyr Ser Thr Thr Pro Asn
210                 215                 220

Ile Leu Asp Pro Val Asn Ala Arg Arg Ala Asp Ala Tyr Ala Gly Tyr
225                 230                 235                 240

Ile Lys Pro Tyr Ile Ser Arg Asn Asn Leu Ala Val Leu Ala Asn His
                245                 250                 255

Thr Val Ser Arg Ile Gln Phe Ala Pro Gln Ser Gly Ser Gln Pro Leu
                260                 265                 270

Arg Ala Thr Gly Val Glu Trp Tyr Pro Thr Gly Asp Lys Ser Gln Lys
                275                 280                 285

Gln Val Leu Asn Ala Arg Tyr Glu Val Ile Leu Ser Ser Gly Ala Ile
                290                 295                 300

Gly Ser Pro Lys Leu Leu Glu Leu Ser Gly Ile Gly Asn Lys Asp Ile
305                 310                 315                 320

Val Ala Ala Ala Gly Ile Gln Ser Leu Leu Asp Leu Pro Gly Val Gly
                325                 330                 335

Ser Asn Met Gln Asp His Val His Ala Val Thr Val Ser Thr Thr Asn
                340                 345                 350

Ile Thr Gly Tyr Thr Thr Asn Ser Ile Phe Thr Asn Asp Ala Leu Ala
                355                 360                 365

Ala Glu Glu Arg Gln Glu Tyr Asp Asn Asn Lys Thr Gly Ile Tyr Thr
                370                 375                 380

Thr Thr Pro Asn Asn Leu Gly Tyr Pro Ser Pro Ser Gln Leu Phe Arg
385                 390                 395                 400

Gly Thr Ser Phe Val Ser Gly Lys Gln Phe Ala Ala Arg Ile Arg Asn
                405                 410                 415

Thr Thr Asp Glu Trp Ala Glu Arg Tyr Ala Ala Asp Asn Ala Thr Asn
                420                 425                 430
```

Ala Glu Leu Leu Lys Lys Gln Tyr Ala Ile Ile Ala Ser Arg Tyr Glu
         435                 440                 445

Glu Asp Tyr Leu Ser Pro Ile Glu Ile Asn Leu Thr Pro Gly Tyr Gly
    450                 455                 460

Gly Thr Ala Asp Val Asp Leu Thr Asn Asn Lys Tyr Gln Thr Val Asn
465                 470                 475                 480

His Val Leu Ile Ala Pro Leu Ser Arg Gly Tyr Thr His Ile Lys Ser
                485                 490                 495

Ala Asp Ile Glu Asp Ala Val Asp Ile Asn Pro Gln Tyr Tyr Ser His
            500                 505                 510

Pro Met Asp Val Asp Val His Val Ala Ser Thr Lys Leu Ala Arg Glu
            515                 520                 525

Ile Ile Ser Ala Ser Pro Gly Leu Gly Asp Ile Asn Ser Gly Glu Thr
        530                 535                 540

Glu Pro Gly Lys Glu Ile Thr Ser Asp Ser Asp Val Arg Lys Trp Leu
545                 550                 555                 560

Ala Asp Asn Val Arg Ser Asp Trp His Pro Val Gly Thr Cys Ala Met
                565                 570                 575

Leu Pro Lys Glu Leu Gly Gly Val Val Asp Pro Asn Leu Lys Val Tyr
            580                 585                 590

Gly Thr Ser Asn Leu Arg Val Val Asp Ala Ser Val Met Pro Leu Glu
        595                 600                 605

Val Ser Ser His Leu Met Gln Pro Thr Phe Gly Ile Ala Glu Lys Ala
610                 615                 620

Ala Asp Ile Ile Lys Ser Ala Asn Lys Lys Arg Ser Asn
625                 630                 635

<210> SEQ ID NO 9
<211> LENGTH: 20
<212> TYPE: DNA
<213> ORGANISM: Artificial Sequence
<220> FEATURE:
<223> OTHER INFORMATION: Synthetic AoOCH1U2kF

<400> SEQUENCE: 9
agcgaccacg cagctccacg                                            20

<210> SEQ ID NO 10
<211> LENGTH: 21
<212> TYPE: DNA
<213> ORGANISM: Artificial Sequence
<220> FEATURE:
<223> OTHER INFORMATION: Synthetic AoOCH1D2kR

<400> SEQUENCE: 10
tctggacgcc gaggggcaca t                                          21

<210> SEQ ID NO 11
<211> LENGTH: 39
<212> TYPE: DNA
<213> ORGANISM: Artificial Sequence
<220> FEATURE:
<223> OTHER INFORMATION: Synthetic AoOCH1D2kiF(NheISbfI)

<400> SEQUENCE: 11
gctagccctg caggagctgg ttcctaccag taccccgcc                       39

<210> SEQ ID NO 12
<211> LENGTH: 25

-continued

<210> SEQ ID NO 12
<211> LENGTH: 25
<212> TYPE: DNA
<213> ORGANISM: Artificial Sequence
<220> FEATURE:
<223> OTHER INFORMATION: Synthetic AoOCH1U2kiR

<400> SEQUENCE: 12
ggtgggaggg ggctgtcgaa gatgc                                    25

<210> SEQ ID NO 13
<211> LENGTH: 36
<212> TYPE: DNA
<213> ORGANISM: Artificial Sequence
<220> FEATURE:
<223> OTHER INFORMATION: Synthetic AOniaD-F(XbaI)

<400> SEQUENCE: 13
tctagaaaca ggccccaaat tcaattaatt gcacct                        36

<210> SEQ ID NO 14
<211> LENGTH: 38
<212> TYPE: DNA
<213> ORGANISM: Artificial Sequence
<220> FEATURE:
<223> OTHER INFORMATION: Synthetic AOniaD-R(SbfI)

<400> SEQUENCE: 14
cctgcaggaa gctttggatt tcctacgtct tcaataca                      38

<210> SEQ ID NO 15
<211> LENGTH: 45
<212> TYPE: DNA
<213> ORGANISM: Artificial Sequence
<220> FEATURE:
<223> OTHER INFORMATION: Synthetic EF1p_IFF

<400> SEQUENCE: 15
cgcggtggcg gccgcgtccg agacagtaag ggattgatct aaatg              45

<210> SEQ ID NO 16
<211> LENGTH: 45
<212> TYPE: DNA
<213> ORGANISM: Artificial Sequence
<220> FEATURE:
<223> OTHER INFORMATION: Synthetic EF1p_IFR

<400> SEQUENCE: 16
gcgcgcacta gttttgtaag atactagaaa gattctgtag agaag              45

<210> SEQ ID NO 17
<211> LENGTH: 45
<212> TYPE: DNA
<213> ORGANISM: Artificial Sequence
<220> FEATURE:
<223> OTHER INFORMATION: Synthetic AmyBt_IFF

<400> SEQUENCE: 17
aaaactagtg cgcgcggatc ggggatctgt agtagctcgt gaagg              45

<210> SEQ ID NO 18
<211> LENGTH: 45
<212> TYPE: DNA
<213> ORGANISM: Artificial Sequence
<220> FEATURE:
<223> OTHER INFORMATION: Synthetic AmyBt_IFR

<400> SEQUENCE: 18

```
tctagaggat cctttcctat aatagactag cgtgcttggc attag            45
```

<210> SEQ ID NO 19
<211> LENGTH: 45
<212> TYPE: DNA
<213> ORGANISM: Artificial Sequence
<220> FEATURE:
<223> OTHER INFORMATION: Synthetic pTN_iF

<400> SEQUENCE: 19

```
aaaggatcct ctagaaacag gccccaaatt caattaattg cacct            45
```

<210> SEQ ID NO 20
<211> LENGTH: 45
<212> TYPE: DNA
<213> ORGANISM: Artificial Sequence
<220> FEATURE:
<223> OTHER INFORMATION: Synthetic pTN_iR

<400> SEQUENCE: 20

```
gcggccgcca ccgcggtgga gctccagctt ttgttccctt tagtg            45
```

<210> SEQ ID NO 21
<211> LENGTH: 593
<212> TYPE: PRT
<213> ORGANISM: Aspergillus oryzae

<400> SEQUENCE: 21

Met Leu Phe Ser Leu Ala Phe Leu Ser Ala Leu Ser Leu Ala Arg Ala
1               5                  10                  15

Ser Pro Ala Gly Arg Ala Lys Asn Thr Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Leu Glu Ala Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Arg Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
    290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
    370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
    530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Cys Ser Thr Leu Tyr
                565                 570                 575

Ala Val Ala Glu Arg Ala Ser Asp Leu Ile Lys Glu Asp Ala Lys Ser
            580                 585                 590

Ala

<210> SEQ ID NO 22
<211> LENGTH: 1782
<212> TYPE: DNA
<213> ORGANISM: Aspergillus oryzae

<400> SEQUENCE: 22
atgctcttct cactggcatt cctgagtgcc ctgtcgctgg ccagggcatc accggctgga      60
cgggccaaga acactacgac atacgactac atcgttgtgg gaggcggcac aagtggtctt     120

-continued

```
gtggtcgcaa atcgcctttc tgagaacccc gatgtctccg ttcttctgct tgaggccggt      180
gcttctgtgt tcaacaaccc ggacgtaacc aacgctaacg gttatggatt ggcctttggc      240
tcggccatcg actggcagta ccagtctatt aaccaaagct atgcaggagg taaacagcaa      300
gttctgcgtg ctggtaaggc ccttggagga accagtacaa tcaatggaat ggcctatacc      360
cgcgcagagg atgtccagat tgacgtttgg cagaaacttg gaaacgaagg ttggacgtgg      420
aaagatctcc taccatacta cctgaagagt gaaaacttga cggccccctac cagctctcag     480 gttgctgctg gcgctgctta taaccctgcc gtgaatggaa agaaggtcc tctcaaggtc       540 ggctggtcga ggagcctggc ctccggtaat ctgtcagttg ctctgaaccg tacgttccaa      600
gccgctggtg ttccatgggt tgaggatgtc aatggaggca gatgcgtgg cttcaacatc       660 tacccatcca ccctcgacgt tgacctcaat gtccgcgaag atgcagcccg gcatactac      720 ttcccttatg atgacaggaa gaaccttcac ctgctggaga acaccactgc caaccgcctt     780
ttctggaaga acggctctgc tgaggaagct attgcggatg tgtcgagat cacctccgct      840 gatggcaagg tcactcgtgt gcatgcaaag aaagaggtca tcatctctgc tggtgccctg     900
cggtctcctc tcattctcga gctttcagga gttggaaacc caaccatcct caaaaagaac     960
aacataaccc cacgtgtcga tctccccacc gttggggaga acctccaaga ccagttcaac    1020
aacggcatgg ctggcgaagg atacggcgtc cttgccggtg cctcaaccgt gacctaccct    1080
tccatctccg acgtcttcgg taacgagact gactctatcg ttgcatctct ccgatctcaa    1140
ctctccgact acgccgccgc gaccgtcaag gtcagcaacg gccacatgaa gcaggaggac    1200
cttgagcgcc tctaccagct ccaatttgac ctcatcgtca aggacaaggt ccctatcgcc    1260
gagatcctct ccacccccgg tggtggaaac gccgtgtcct ccgaattctg gggcttgctt    1320
cccttcgccc gtggcaacat ccacattagc tccaatgacc cgactgctcc cgccgccatc    1380
aaccctaact actttatgtt cgaatgggac ggcaagagcc aggccggtat cgccaagtac    1440
atcaggaaga ttctccgcag cgcaccattg aacaaactta ttgcgaagga aaccaagccc    1500
ggtctctctg agattccggc cactgctgcg gatgagaagt gggttgaatg gctcaaggct    1560
aactatcgtt ccaacttcca ccccgtcgga actgctgcca tgatgcctcg ttccattggt    1620
ggcgttgttg ataaccgtct ccgggtctat ggtaccagca atgttcgcgt cgtagatgcg    1680
tctgtcctgc ccttccaggt ttgcggccac ttgtgcagca cgctttatgc cgttgccgag    1740
cgcgcttccg acttgattaa ggaggatgcg aagagtgctt ag                        1782
```

<210> SEQ ID NO 23
<211> LENGTH: 30
<212> TYPE: DNA
<213> ORGANISM: Artificial Sequence
<220> FEATURE:
<223> OTHER INFORMATION: Synthetic AoFADGDH_F_SpeI

<400> SEQUENCE: 23

```
actagtatgc tcttctcact ggcattcctg                                         30
```

```
<210> SEQ ID NO 24
<211> LENGTH: 31
<212> TYPE: DNA
<213> ORGANISM: Artificial Sequence
<220> FEATURE:
<223> OTHER INFORMATION: Synthetic AoFADGDH_R_speI

<400> SEQUENCE: 24
actagtctaa gcactcttcg catcctcctt a                                31
```

FAD-DEPENDENT GLUCOSE DEHYDROGENASE

CROSS-REFERENCE TO RELATED APPLICATIONS

This patent application is a continuation-in-part of copending International Patent Application No. PCT/JP2016/050913, filed on Jan. 14, 2016, which claims the benefit of Japanese Patent Application No. 2015-006383, filed Jan. 16, 2015, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 47,156 bytes ASCII (Text) file named "730311ReplacementSequenceListing.txt," created Jun. 2, 2020.

TECHNICAL FIELD

The present invention relates to FAD-dependent glucose dehydrogenase, a glucose sensor comprising the FAD-dependent glucose dehydrogenase, and a method for measuring glucose concentration using them.

BACKGROUND ART

Measurement of blood glucose concentration is essential for diabetic patients to suitably control their blood sugar levels. For daily checking of blood sugar levels, for example, glucose sensors and simple blood glucose self-monitoring kits using glucose oxidase (also referred to as "GOD" in the present specification) or glucose dehydrogenase (also referred to as "GDH" in the present specification) are used. GOD has been used for a long time as a blood sugar measurement enzyme; however, since dissolved oxygen affects the measured values, GDH has mainly been used in recent years. A glucose sensor using GDH as a raw material is to measure glucose concentration in blood using the following reaction of GDH:

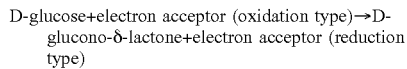

That is, glucose can be qualitatively analyzed by measuring the flow of electrons generated by the oxidation of glucose. As GDH that has been used for blood sugar measurement, the following three types, due to the difference in the coenzyme required for the reaction, are known: nicotinamide-dependent GDH, pyrroloquinoline quinone (also referred to as "PQQ" in the present specification)-dependent GDH, and flavin adenine dinucleotide (also referred to as "FAD" in the present specification)-dependent GDH. As the nicotinamide-dependent GDH, those derived from the genus *Bacillus* are commercially available. However, they cannot be purified in the form of holoenzymes containing coenzymes, and it is thus necessary to add nicotinamide adenine dinucleotide (also referred to as "NAD" in the present specification) or the like that serves as a coenzyme in the production of the sensor. Such a complication and the expensiveness of NAD and the like serving as coenzymes are problematic. In contrast, the PQQ-dependent GDH can be supplied in the form of a holoenzyme, and is advantageous in that its specific activity is high and sufficient response signals for glucose can be obtained; however, lack of stringency of substrate specificity and reactivity with sugars other than glucose, such as maltose, are regarded as problems. The FAD-dependent GDH has become more widespread as GDH that can overcome these problems.

As the FAD-dependent glucose dehydrogenase (also referred to as "FADGDH" in the present specification), those derived from the genus *Aspergillus* (PTL 1, PTL 2, and PTL 7), those derived from the genus *Penicillium* (PTL 3), those derived from filamentous fungi of the Mucoraceae (PTL 4 to PTL6), and the like are known. Further, glucose sensors (blood sugar sensors) using such GDH are also known.

CITATION LIST

Patent Literature

PTL 1: JP4494978B
PTL 2: JP4292486B
PTL 3: U.S. Pat. No. 7,494,494
PTL 4: JP4648993B
PTL 5: JP2013-90621A
PTL 6: JP2013-116102A
PTL 7: WO2006/101239

SUMMARY OF INVENTION

Technical Problem

An object of the present invention is to provide more excellent FADGDH, to construct a more excellent glucose sensor using the FADGDH, and to provide a method for measuring glucose concentration using them.

Solution to Problem

The present inventors examined the characteristics of glucose sensors using various types of FADGDH in various ways. As a result, the present inventors found an important problem in that glucose sensors produced using FADGDH having sugar chains showed difference in their electrode response values.

The present inventors further conducted studies, and found that the difference in the electrode response values was attributable to the uniformity of the molecular weight of FADGDH used in glucose sensors. The present inventors also found that the proportional relationship between the glucose concentration and the response values of glucose sensors was maintained at a high concentration by increasing the uniformity of the molecular weight of FADGDH used in the glucose sensors.

The present invention has been completed based on these findings, and is set forth in the following items 1 to 4.

Item 1.

FAD-dependent glucose dehydrogenase in which the range of molecular weight distribution observed by SDS-PAGE is within 50 kDa when viewed in a molecular weight distribution in which the relative value of band intensity exceeds 60% of the maximum value.

Item 2.

The FAD-dependent glucose dehydrogenase according to Item 1, which is derived from a microorganism selected from any one of the following genera:

*Aspergillus, Trichoderma, Neurospora, Monascus, Fusarium, Saccharomyces, Pichia, Candida, Schizosaccha-* romyces *Cryptococcus, Schizophyllum, Mucor, Absidia, Actinomucor, Colletotrichum, Circinella*, and *Arthrinium*.

Item 3.

A glucose sensor comprising the FAD-dependent glucose dehydrogenase according to Item 1 or 2.

Item 4.

A method for measuring glucose concentration using the FAD-dependent glucose dehydrogenase according to Item 1 or 2, or the glucose sensor according to Item 3.

Advantageous Effects of Invention

The present invention can provide a glucose sensor having excellent performance, and also provide GDH suitable for the glucose sensor.

BRIEF DESCRIPTION OF DRAWINGS

FIG. 1 shows the results of comparison of the identity of amino acid sequences of och1 orthologs in various *Aspergillus* species.

FIG. 2 shows a process of disrupting the och1 gene of *Aspergillus oryzae*.

FIG. 3 shows a vector map of *Aspergillus oryzae*-expressing plasmid pTNE-AomFADGDH.

DESCRIPTION OF EMBODIMENTS

FADGDH

Figure 4:
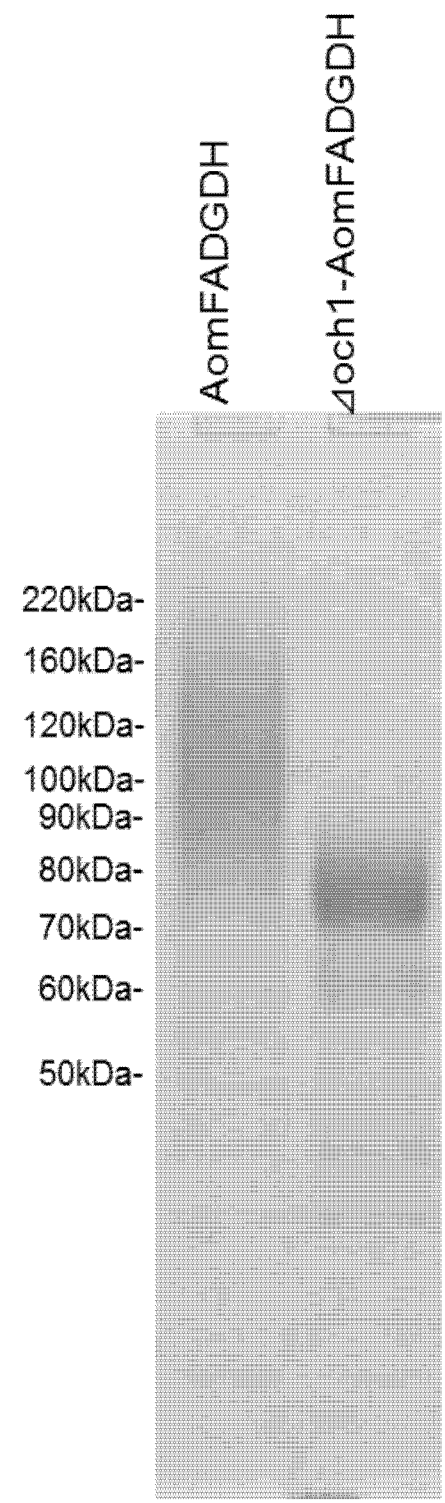
FIG. 4 shows the results of SDS-PAGE of purified enzymes AomFADGDH and Δoch1-AomFADGDH.

One embodiment of the present invention is FADGDH in which the range of molecular weight distribution observed by SDS-PAGE is within 50 kDa when viewed in a molecular weight distribution in which the relative value of band intensity exceeds 60% of the maximum value.

In the present invention, the molecular weight distribution is determined by SDS-PAGE. Specifically, the molecular weight distribution is determined according to the following steps (1) to (4):

(1) SDS-PAGE is performed using Nu-PAGE 4-12% Bis-Tris Gel (produced by Invitrogen) by applying a molecular weight marker (BenchMark™ Protein Ladder) having a molecular weight ladder of 50, 60, 70, 80, 90, 100, 120, 160, and 220 kDa.

(2) The shade of the band shown in the results of SDS-PAGE in step (1) above is scanned. The molecular weight is plotted on the horizontal axis, and the relative intensity of the band is plotted on the vertical axis. For scanning and plotting, Gel Pro analyzer (produced by Nippon Roper K.K.) is used.

(3) A molecular weight range in which the relative value of band intensity exceeds 60% of the maximum value is read from the results plotted in step (2) above.

(4) The molecular weight distribution of the present invention is expressed by separating the minimum range of molecular weight including the molecular weight range read in step (3) above by each molecular weight set in the ladder of the molecular weight marker used in step (1) above. For example, when the molecular weight range read in step (3) above is 75-85 kDa, the molecular weight distribution is 70-90 kDa; and when the molecular weight range is 85-105 kDa, the molecular weight distribution is 80-120 kDa.

The range of molecular weight distribution of the FADGDH of the present invention is within 50 kDa when measured in the above manner. The range of molecular weight distribution is preferably within 40 kDa, more preferably within 30 kDa, and even more preferably within 20 kDa.

The origin of the FADGDH of the present invention is not particularly limited; however, the FADGDH of the present invention is preferably derived from a microorganism selected from any one of the following group (A):

(A) the genera *Aspergillus, Trichoderma, Neurospora, Monascus, Fusarium, Saccharomyces, Pichia, Candida, Schizosaccharomyces, Cryptococcus, Schizophyllum, Mucor, Absidia, Actinomucor, Colletotrichum, Circinella*, and *Arthrinium*.

The FADGDH of the present invention is more preferably derived from a microorganism selected from any one of the following group (B):

(B) the genera *Aspergillus, Mucor, Absidia, Actinomucor, Colletotrichum, Circinella, Arthrinium*, and *Penicillium*.

The FADGDH of the present invention is even more preferably derived from any microorganism selected from the group consisting of the genera *Aspergillus, Mucor*, and *Circinella*. Examples of such microorganisms include *Aspergillus oryzae* (SEQ ID NO: 3), *Aspergillus terreus* (SEQ ID NO: 4), *Mucor prainii* (SEQ ID NO: 5), *Mucor hiemalis* (SEQ ID NO: 6), *Mucor subtilissimus* (SEQ ID NO: 7), *Circinella simplex* (SEQ ID NO: 8), and the like.

The FADGDH of the present invention is still more preferably derived from a microorganism of the genus *Aspergillus*. The FADGDH of the present invention is further still more preferably derived from one microorganism of Aspergillus oryzae or *Aspergillus terreus*.

The FADGDH of the present invention may be obtained by adding alterations to the amino acid sequence etc. of each of the above microorganisms, to an extent in which the function as FADGDH is not lost. When the amino acid sequence is altered, the degree of alteration is not particularly limited. Examples of alternations include substitution, deletion, insertion, and/or addition of one or more amino acids. The amino acid sequence may have 70% (preferably 75%, more preferably 80%, even more preferably 85%, still more preferably 90%, still more preferably 95%, still more preferably 98%, and still more preferably 99%) or more identity to a wild-type amino acid sequence.

The sugar chain content of the FADGDH of the present invention is preferably more uniform than those produced by wild-type microorganisms. The degree of uniformity is expressed in terms of the range of molecular weight distribution. The range of molecular weight distribution measured in the above-described method is within 50 kDa. The range of molecular weight distribution is preferably within 40 kDa, more preferably within 30 kDa, and even more preferably within 20 kDa.

The sugar chain content of the FADGDH of the present invention is preferably reduced from those produced by wild-type microorganisms. The degree of reduction is not particularly limited, but is preferably 60% or less, more preferably substantially the same as or less than 56.3% (in the present specification, the phrase "substantially the same" refers to an indistinguishable state, in consideration of variation in the measurement etc.), even more preferably substantially the same as or less than 55%, still more preferably substantially the same as or less than 51.5%, and still more preferably substantially the same as or less than 44.0%, compared with those of wild-type microorganisms.

In the present specification, the sugar chain content of the FADGDH is determined in the following manner. The molecular weight of the entire FADGDH (including both the polypeptide chain portion and the sugar chain portion) and the molecular weight of only the polypeptide chain portion of the FADGDH (which can be calculated from the amino acid sequence) are determined. Then, the molecular weight of only the polypeptide chain portion of the FADGDH is subtracted from the molecular weight of the entire FADGDH. The resulting value is regarded as the molecular weight of the sugar chain portion. This value is divided by the molecular weight of the entire FADGDH to thereby determine the sugar chain content.

In the present specification, the molecular weight is determined according to the following steps (1), (2), and (5) to (7):

(1) SDS-PAGE is performed using Nu-PAGE 4-12% Bis-Tris Gel (produced by Invitrogen) by applying a molecular weight marker (BenchMark™ Protein Ladder) having a molecular weight ladder of 50, 60, 70, 80, 90, 100, 120, 160, and 220 kDa.

(2) The shade of the band shown in the results of SDS-PAGE in step (1) above is scanned. The molecular weight is plotted on the horizontal axis, and the relative intensity of the band is plotted on the vertical axis. For scanning and plotting, Gel Pro analyzer (produced by Nippon Roper K.K.) is used.

(5) A molecular weight in which the relative intensity of the band is highest is read from the results plotted in step (2) above.

(6) The minimum range of molecular weight including the molecular weight range read in step (5) above is separated by each molecular weight set in the ladder of the molecular weight marker used in step (1) above. For example, when the molecular weight in which the relative intensity of the band is highest read in step (5) above is 76 kDa, the range of molecular weight is 70-80 kDa.

(7) The central value of the range of molecular weight (a value obtained by adding the upper limit and lower limit of the range, and dividing the resulting value by 2) shown in step (6) above is used as the molecular weight.

Moreover, the molecular weight of the FADGDH of the present invention is preferably reduced from those produced by wild-type microorganisms, as a result of the decrease in the sugar chain content as described above. The degree of reduction is not particularly limited, but is preferably 88% or less, more preferably 83% or less, even more preferably 75% or less, still more preferably 70% or less, still more preferably substantially the same as or less than 69.7%, still more preferably substantially the same as or less than 68.2%, still more preferably substantially the same as or less than 65%, and still more preferably substantially the same as or less than 60.7%, compared with those of wild-type microorganisms.

Furthermore, the molecular weight of the FADGDH of the present invention is preferably 100 kDa or less, more preferably 90 kDa or less, even more preferably substantially the same as or less than 88 kDa, and still more preferably the same as or less than 85 kDa. In one embodiment, the molecular weight of the FADGDH is 65 kDa or more, 70 kDa or more, or 75 kDa or more.

The FADGDH of the present invention described above can take the form of a suitable composition, in consideration of the application thereof to a glucose sensor, a glucose measurement method, etc., described later. The form of the composition is not particularly limited, and may be in a dried state (e.g., a freeze-dried form or a powder form) or a liquid state. Methods for producing such compositions have already been established in this technical field. Therefore, a person skilled in the art can produce the composition of the present invention by applying these findings, and embodiments thereof are not particularly limited. Examples of substances that can be added to the composition include various substances listed in the present specification as examples of substances that may be contained in a glucose sensor described later.

As shown in Examples provided later, when the FADGDH of the present invention is used in a glucose sensor, an excellent proportional relationship of response values to the actual glucose concentration is ensured in a higher glucose concentration range, compared with when wild-type FADGDH is used. One reason for this is considered to be as follows. Because the activity per weight of glycoprotein is enhanced due to the decrease in the sugar chain content, enzyme activity is relatively higher, even though the same weight of glycoprotein is mounted in a sensor, resulting in sufficient response for a high concentration of glucose.

Moreover, it is expected for the FADGDH obtained by the production method of the present invention that the uniform sugar chain content leads to higher efficiency in steps, such as chromatography, in the purification stage of the enzyme, consequently increasing the purification yield.

Glucose Sensor

One embodiment of the present invention is a glucose sensor comprising the FADGDH described above.

The glucose sensor is not particularly limited, as long as it comprises the FADGDH of the present invention. For example, the enzyme of the present invention is immobilized on an electrode, such as a carbon electrode, a gold electrode, or a platinum electrode. Examples of methods for immobilization include a method using a crosslinking reagent, a method for encapsulating the FADGDH in a polymer matrix, a method for covering the FADGDH with a dialysis membrane, methods using a photo-crosslinkable polymer, a conductive polymer, a redox polymer, etc. Alternatively, the FADGDH of the present invention may be immobilized in a polymer or immobilized adsorptively on an electrode, together with a coenzyme, such as NAD or NADP; or an electron mediator, such as ferrocene or its derivatives. These methods may also be used in combination. Typically, the FADGDH of the present invention is immobilized on a carbon electrode using glutaraldehyde, followed by treatment with an amine-containing reagent. In this manner, the glutaraldehyde can be blocked. The electron mediator to be used is one that can receive electrons from FAD, which is a coenzyme of GDH, and that can supply electrons to coloring substances and electrodes. Examples include, but are not limited to, ferricyanide salts, phenazine ethosulfate, phenazine methosulfate, phenylenediamine, N,N,N',N'-tetramethylphenylenediamine, 1-methoxyphenazine methosulfate, 2,6-dichlorophenolindophenol, 2,5-dimethyl-1,4-benzoquinone, 2,6-dimethyl-1,4-benzoquinone, 2,5-dichloro-1,4-benzoquinone, nitrosoaniline, ferrocene derivatives, osmium complexes, ruthenium complexes, and the like. The GDH composition on the electrode may contain proteins, such as bovine serum albumin and sericin, as a stabilizer and/or an activator; surfactants, such as TritonX-100, Tween20, cholate, and deoxycholate; amino acids, such as glycine, serine, glutamic acid, glutamine, aspartic acid, asparagine, and glycylglycine; sugars and/or sugar alcohols, such as trehalose, inositol, sorbitol, xylitol, glycerol, and sucrose; and inorganic salts, such as sodium chloride and potassium chloride; and may further contain hydrophilic polymers, such as pullulan, dextran, polyethylene glycol, polyvinylpyrrolidone, carboxymethylcellulose, and polyglutamic acid.

Glucose Measurement Method

One embodiment of the present invention is a method for measuring glucose concentration using the FADGDH or glucose sensor described above. Methods for measuring glucose using glucose dehydrogenase have already been established in this technical field. Therefore, the amount or concentration of glucose in various samples can be measured by using the FADGDH of the present invention according to known methods. The mode for the measurement is not particularly limited, as long as the FADGDH of the present invention is used to measure the amount or concentration of glucose. For example, the measurement may be performed by causing the FADGDH of the present invention to act on glucose in a sample, and spectrophotometrically measuring the structural change of the electron acceptor (e.g., DCPIP) associated with glucose dehydrogenation. The sample containing glucose is not particularly limited. Examples of the sample include blood, beverages, foods, and the like. The amount of enzyme added to the sample is not particularly limited, as long as it is possible to measure the amount or concentration of glucose.

The glucose concentration can be measured using the glucose sensor described above in the following manner. A buffer solution is placed in a thermostatic cell, and the temperature is maintained constant. Potassium ferricyanide, phenazine methosulfate, or the like may be used as a mediator. An electrode on which the FADGDH of the present invention is immobilized is used as a working electrode. Further, a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

The glucose measurement method of the present invention can also be performed using, other than the above glucose sensor, a reagent, a kit, and the like for measuring blood glucose concentration, such as a composition for glucose measurement, a glucose assay kit, etc.

The composition for glucose measurement and the glucose assay kit are not particularly limited, as long as they contain the FADGDH of the present invention in an amount sufficient for at least one assay. The kit typically contains the FADGDH of the present invention, a buffer solution, a mediator, and like reagents required for the measurement, a glucose standard solution for preparing a calibration curve, and instructions for use. The kit of the present invention may be provided as, for example, a freeze-dried reagent or a solution in an appropriate storage solution.

Utilization methods, production methods, etc., of the glucose sensor, composition for glucose measurement, glucose assay kit, etc., have already been established in this technical field. Therefore, a person skilled in the art can produce and use glucose sensors, glucose measurement reagents, glucose measurement kits, etc., by applying those findings, and embodiments thereof are not particularly limited. Usable examples include products constituting the whole or a part of one set that is used to measure glucose concentration using FADGDH, the products containing the FADGDH of the present invention.

Method for Producing FADGDH of the Present Invention

The method for producing the FADGDH of the present invention (FADGDH in which the range of molecular weight distribution observed by SDS-PAGE is within 50 kDa when viewed in a molecular weight distribution in which the relative value of band density exceeds 60% of the maximum value) is not particularly limited.

For example, the uniformity of the molecular weight can be increased by a known technique that can control alterations of the structure of sugar chains to be added to proteins. Examples of the technique are shown below.

Two types of sugar chains attached to proteins are known: N-type sugar chains attached to asparagine residues of proteins, and O-type sugar chains attached to serine or threonine. Of these, there have been many findings and detailed analyses regarding the biosynthetic pathway of N-type sugar chains.

The biosynthesis of sugar chains first starts in the endoplasmic reticulum (ER), and then modification of sugar chains further occurs in the Golgi body. It has been found that, among these, sugar chains produced in the ER are basically common in fungi and mammalian cells. The sugar chains have a core structure (Man8GlcNAc2) comprising 8 molecules of mannose (Man) and 2 molecules of N-acetylglucosamine (GlcNAc). Proteins with such core structure sugar chains are transported to the Golgi body, and subjected to various modifications.

In yeast, in the production process of sugar chains in the ER, alg family genes perform synthesis. First, GlcNAc is added by alg7, alg13, and alg14 genes, and then mannose is added by alg1, alg2, alg11, alg3, and alg9, thereby forming a core structure. Next, to glycoproteins transported to the Golgi body, mannose is further added by och1, and then a large amount of mannose is added by Mnn1, Mnn4, and Mnn6, thereby forming hypermannose-type sugar chains.

There are attempts to alter the structure of sugar chains attached to proteins secreted in yeast and filamentous fungi by gene disruption, as described above, using a genetic engineering approach. For example, Appl Environ Microbiol. 2008 74(4): 1076-86, shows that when the alg3 (algC) gene of filamentous fungi *Aspergillus niger* and *Aspergillus nidulans* was disrupted, the amount of hexose contained in N-type sugar chains was reduced. It was also examined that the alg3 gene encoded α1,3-mannosyltransferase. Furthermore, PLoS One 2010 5(12), examined that the sugar chain composition of *Aspergillus fumigatus* was changed by disrupting the och1 gene.

Meanwhile, regarding filamentous fungi, J Biol Chem. 2009 284(18):11900-12, examined that in yeast *Saccharomyces cerevisiae*, G377R-mutants of alg2 were sensitive to temperature, and that the sugar chain length was significantly reduced. Further, Glycobiology 1999 9 (12):1287-93 has reported that alg2 mutant was obtained in *Rhizomucor pusillus*. It was examined that almost all N-type sugar chains of the mutant, in which the function of alg2 was reduced by insertion mutation of 5 bp, had Man1GlcNAc2 or Man2GlcNAc2 structure.

In addition, the FADGDH of the present invention can be produced by a method for producing FADGDH using modified microorganisms in which the function of the och1 gene is reduced, as described below.

The och1 gene regulates the expression of och1, which is an enzyme involved in the biosynthesis of N-type sugar chains attached to asparagine residues of proteins.

The och1 gene is present in almost all microorganisms having the function of synthesizing glycoproteins. Examples include, but are not limited to, the genera *Aspergillus, Trichoderma, Neurospora, Monascus, Fusarium, Saccharomyces, Pichia, Candida, Schizosaccharomyces, Cryptococcus, Schizophyllum, Mucor, Absidia, Actinomucor, Colletotrichum, Circinella, Arthrinium, Coccidioides, Botryotinia, Leptosphaeria, Podospora, Thielavia, Verticillium, Yarrowia, Cyberlindnera, Scheffersomyces, Eremothecium, Debaryomyces, Saccharamycetaceae, Ashbya, Kluyveromyces, Lachancea, Zygosaccharomyces, Kazachstania, Torulaspora, Naumovozyma, Tetrapisispora, Myceliophthora*, and the like.

The present inventors analyzed in more detail the influence of the sugar chain content of FADGDH on electrode response values in a glucose sensor using various microorganisms having the ability to produce FADGDH. As a result, in purified enzymes purified from a culture medium obtained by expressing FADGDH in *Aspergillus oryzae*, which was used as a host, and growing the host by liquid culture, attached sugar chains had non-uniform compositions. It was assumed that sugar chains of various lengths were attached.

Moreover, it was confirmed that in FADGDH expressed in yeast *Saccharomyces cerevisiae* as a host, sugar chains of various lengths were attached, as with FADGDH expressed in *Aspergillus oryzae* as a host, and that the length of the sugar chains was longer than that of FADGDH expressed in *Aspergillus oryzae* as a host.

Then, the present inventors further conducted extensive research to adjust the content of sugar chains attached to FADGDH. As a result, the present inventors found that sugar chains attached to FADGDH could be significantly shortened (to thereby reduce the sugar chain content) by disrupting och1 gene, which is a gene involved in sugar chain synthesis in microorganisms having the ability to produce FADGDH, or by reducing the function of the och1 gene, and that the sugar chain composition was almost uniform.

More preferable means for reducing the function of the och1 gene of microorganisms is to disrupt a DNA corresponding to the och1 gene.

In the method for producing the FADGDH of the present invention described above, the sequence of the och1 gene is not particularly limited. Examples of the sequence derived from *Aspergillus oryzae* include a DNA sequence of SEQ ID NO: 2. SEQ ID NO: 2 is a DNA sequence encoding the amino acid sequence of SEQ ID NO: 1.

The sequence of och1 gene varies depending on the type of microorganism. For example, the sequence is highly conserved among microorganisms of the genus *Aspergillus*. Moreover, a homology search has confirmed that microorganisms other than the genus *Aspergillus* have sequences with high homology (E-value <2e-34 (minus 34th power of 2; in this specification, "2e-n" represents minus n-th power of 2) in the genera *Coccidioides, Botryvotinia, Leptosphaeria, Podospora, Thielavia, Verticillium, Fusarium, Yarrowia, Neurospora, Cyberlindnera, Pichia, Candida, Scheffersomyces, Eremothecium, Debarvomyces, Saccharomycetaceae, Ashbya, Kluyveromyces, Lachancea, Zygosaccharomyces, Saccharomyces, Kazachstania, Torulaspora, Naumovozyma, Tetrapisispora, Naumovozyma, Schizosaccharomyces, Kazachstania, Eremothecium*, and *Myceliophthora* (Tables 1 and 2 show the results). This indicates that the sequence of the och1 gene is highly conserved in fungi.

TABLE 1

| Description | E value | Accession |
|---|---|---|
| *Aspergillus oryzae* RIB40 DNA, SC113 | 0 | AP007166.1 |
| *Aspergillus oryzae* RIB40 alpha-1,6-mannosyltransferase subunit (Och1), mRNA | 0 | XM_001823900.2 |
| *Aspergillus flavus* NRRL3357 alpha-1,6-mannosyltransferase subunit (Och1), putative, mRNA | 0 | XM_002380971.1 |
| *Aspergillus oryzae* cDNA, contig sequence: AoEST0461 | 0 | AB223822.1 |
| *Aspergillus clavatus* NRRL 1 alpha-1,6-mannosyltransferase subunit (Och1), putative (ACLA_011950), partial mRNA | 1E−176 | XM_001274192.1 |
| *Aspergillus terreus* NIH2624 hypothetical protein (ATEG_05779) partial mRNA | 2E−175 | XM_001214957.1 |
| *Aspergillus niger* contig An07o0130, genomic contig | 1E−171 | AM270131.1 |
| *Aspergillus niger* CBS 51388 alpha-1,6-mannosyltranssferase subunit (Och1), mRNA | 3E−171 | XM_001391540.2 |
| *Aspergillus fumigatus* Af293 alpha-1,6-mannosyltransferase subunit (Och1) (AFUA_5G08580),partial mRNA | 1E−163 | XM_748686.1 |
| *Aspergillus fumigatus* mRNA for mannosyltransferase (Och1 gene), strain D141 | 2E−162 | FR667640.1 |
| *Neosartorya fischeri* NRRL 181 alpha-1,6-mannosyltransferase subunit (Och1), putative NFIA_078700) partial mRNA | 1E−157 | XM_001259826.1 |
| TPA: *Aspergillus nidulans* FGSC A4 chromosome III | 1E−150 | BN001303.1 |
| *Aspergillus nidulans* FGSC A4 hypothetical protein AN4716.2 partial mRNA | 5E−150 | XM_657228.1 |
| *Penicillium chrysogenum* Wisconsin 54-1255 complete genome, contig Pc00c22 | 3E−114 | AM920437.1 |
| *Penicillium chrysogenum* Wisconsin 54-1255 hypothetical protein (Pc22g16540) mRNA, complete cds | 1E−113 | XM_002565522.1 |
| *Coccidioides posadasii* C735 delta SOWgp initiation-specific alpha-1,6-mannosyltransferase, putative, mRNA | 4E−94 | XM_003069965.1 |
| *Coccidioides posadasii* mannosyltransferase-like protein mRNA, partial cds | 4E−94 | DQ133453.1 |
| *Coccidioides immitis* RS hypothetical protein (CIMG_06774) partial mRNA | 3E−89 | XM_001242877.1 |
| *Trichophyton verrucosum* HKI 0517 glycosul transferase, putative, mRNA | 2E−78 | XM_003023395.1 |
| *Cladophialphera carrionii* CBS 160.54 hypothetical protein partial mRNA | 3E−76 | XM_008729120.1 |
| *Ajellomyces dermatitidis* SLH14081 alpha-1,6-mannosyltransferase subunit, mRNA | 6E−73 | XM_002628191.1 |
| *Cladophialophera yegresii* CBS 114405 alpha 1,6-mannosyltransferase partial mRNA | 2E−72 | XM_007757612.1 |
| *Phaeosphaeria nodorum* SN15 hypothetical protein partial mRNA | 2E−72 | XM_001793481.1 |
| *Trichophyton rubrum* CBS 118892 alpha-1,6-mannosyltransferase (TERG_07870) mRNA, complete cds | 7E−72 | XM_003231522.1 |

TABLE 1-continued

| Description | E value | Accession |
|---|---|---|
| *Arthroderme banhamiae* CBS 112371 glycosyl transferase, putative, mRNA | 9E-71 | XM_003014840.1 |
| *Neofusicoccum parvum* UCRNP2 putative initiation-specific alpha- -mannosyltransferase protein mRNA | 2E-67 | XM_007583042.1 |
| *Cyphellophore europaea* CBS 101466 hypothetical protein partial mRNA | 6E-67 | XM_008719566.1 |
| *Uncinocarpus reesii* 1704 conserved hypothetical protein, mRNA | 6E-67 | XM_002544127.1 |
| *Leptosphaeria biglobosa brassicae* b35_scaffold00003 complete sequence | 8E-65 | FO905661.1 |
| *Baudoinia compniacensis* UAMH 10762 glycosultransferase family 32 protein partial mRNA | 3E-64 | XM_007680626.1 |
| *Coniosporium apollinis* CBS 100218 alpha 1,6-mannosyltransferase partial mRNA | 1E-63 | XM_007782782.1 |
| *Marssonina brunnea* f. sp. 'multigermtubi' MB_m1 glycosyltransferase sugar-binding region containing DXD domain-containing protein (MBM_07558), mRNA | 2E-61 | XM_007295385.1 |
| *Leptosphaeria maculans lepidii* ibcn84_scaffold00002 complete sequence | 5E-61 | FO906022.1 |
| *Arthroderma gypseum* CBS 118893 initiation-specific alpha-1,6-mannosyltransferase (MGYG_04455; mRNA, complete cds | 7E-60 | XM_003174230.1 |
| *Cladophielophora psammophile* CBS 110553 alpha 1,6-mannosyltransferase partial mRNA | 2E-59 | XM_007740723.1 |

TABLE 2

| Description | E value | Accession |
|---|---|---|
| *Endocarpon pusillum* Z07020 hypothetical protein mRNA | 3E-58 | XM_007806832.1 |
| *Leptosphaeria maculans brassicae* wa74, scaffold00486 complete sequence | 1E-57 | FC906600.1 |
| *Leptosphaeria maculans* JN3 SuperContig_0_v2 | 1E-57 | NW_003533878.1 |
| *Glarea lozoyansis* ATCC 20868 hypothetical protein mRNA | 3E-57 | XM_008079800.1 |
| *Leptoshaperia maculans* JN3 hypothetical protein (LEMA_P012520.1) mRNA, complete cds | 3E-57 | XM_003845896.1 |
| *Pyrenophora tritici-repentis* Pt-1C-BFP initiation-specific alpha-1,6-mannosyltransferase, mRNA | 3E-57 | XM_001932482.1 |
| *Setosphaeria turcica* Et28A glycosyltransferase family 32 protein partial mRNA | 1E-56 | XM_008028936.1 |
| *Capronia epimyces* CBS 606.96 alpha 1,6-mannosyltransferase partial mRNA | 4E-56 | XM_007738054.1 |
| *Pseudocercospora fijiensis* CIRAD86 glycosyltransferase family 32 protein mRNA | 2E-54 | XM_007926821.1 |
| *Colletotrichum gloeosporioides* Nare gcij initiation-specific alpha-mannosyltransferase (CGGC5_1162), partial mRNA | 2E-54 | XM_007281274.1 |
| *Sclerotinia sclerotiorum* 1980 hypothetical protein (SSIG_03158) partial mRNA | 2E-54 | XM_001595020.1 |
| *Exophiale dermatitidis* NIH/LIT8856 alpha 1,6-mannosyltransferase partial mRNA | 4E-50 | XM_009159118.1 |
| *Arthroderma otae* CBS 113480 alpha 1,6 mannosyltransferase, mRNA | 4E-50 | XM_002848638.1 |
| *Chaetomium globosum* CBS 148.51 hypothetical protein (CHGG_06214) partial mRNA | 4E-50 | XM_001222308.1 |
| *Gaeumannomyces graminis* var. *tritici* R3-111a-1 initiation-specific alpha-1,6- mannosyltransferase mRNA | 1E-49 | XM_009229841.1 |
| *Verticillium dahliae* JR2 chromosome 1. complete sequence | 5E-49 | CP009075.1 |
| *Botryotinia fuckeliana* T4 SuperContig. 109_1 genomic supercontig | 5E-49 | FQ790338.1 |
| *Paracoccidioides brasiliensis* Pb18 hypothetical protein partial mRNA | 2E-48 | XM_010764512.1 |
| *Capronia coronata* CBS 617.96 alpha 1,6-mannosyltransferase partial mRNA | 2E-48 | XM_007729544.1 |
| *Pyrenophora teres* f. *teres* 0-1 hypothetical protein, mRNA | 2E-48 | XM_003298418.1 |
| *Paracoccidioides brasiliensis* Pb01 initiation-specific alpha-1,6-mannosyltransferase, mRNA | 2E-48 | XM_002793733.1 |
| *Verticillium dahliae* VdLs, 17 initiation-specific alpha-1,6-mannosyltransferase partial mRNA | 6E-48 | XM_009653473.1 |
| *Leptosphaeria biglobose* Thlaspii ibon65_scaffold00032 complete sequence | 2E-46 | FO905869.1 |
| *Colletotrichum ficriniae* PJ7 glycosyltransferase sugar-binding region containing DXD domain-containing protein mRNA | 1E-44 | XM_007592532.1 |
| *Verticillium albo-atrum* VaMs.102 initiation-specific alpha-1,6-mannosyltransferase, mRNA | 1E-44 | XM_003008115.1 |
| *Bipolaris zeicola* 26-R-13 glycosyltransferase family 32 protein partial mRNA | 4E-44 | XM_007720195.1 |
| *Bipolaris oryzae* ATCC 44560 glycosyltransferase family 32 protein partial mRNA | 4E-43 | XM_007686969.1 |
| *Eutypa iata* UCREL1 putative initiation-specific alpha- -mannoyltransferase protein mRNA | 2E-42 | XM_007790568.1 |
| *Magnaporthe oryzae* 70-15 initiation-specific alpha-1,6-mannosyltransferase (MGG_02859) mRNA, complete cds | 2E-42 | XM_003720828.1 |
| *Talaromyces stipitatus* ATCC 10500 alpha-1,6-mannosyltransferase subunit (Och1), putative, mRNA | 2E-41 | XM_002481563.1 |
| *Penicillium marnaffei* ATCC 18224 alpha-1,6-mannosyltransferase subunit (Och1), putative, mRNA | 3E-38 | XM_002147438.1 |
| *Cochliobolus sativus* NO90Pr glycosyltransferase family 32 protein mRNA | 1E-37 | XM_007705399.1 |
| *Myceliophthora thermophila* ATCC 42464 glycosyltranferase family 32 protein (MYCTH_2297411) mRNA, complete cds | 2E-35 | XM_003659835.1 |
| *Myceliophthora thermophila* ATCC 42464 chromosome 1, complete sequence | 2E-35 | CP003002.1 |

Base sequence identity is calculated using the default (initial) parameter in the homology algorithm BLAST of the National Center for Biotechnology Information (NCBI). "E-value" is a scale for comparing the similarity of two sequences. A smaller value indicates a higher similarity.

In the method for producing the FADGDH of the present invention shown above, the och1 gene may be the following (a) or (b):

(a) a DNA encoding an amino acid sequence having 68% or more (preferably 70% or more, more preferably 75% or more, even more preferably 80% or more, still more preferably 85% or more, further even more preferably 90% or more, further still more preferably 95% or more, further still more preferably 98% or more, and further still more preferably 99% or more) identity to the amino acid sequence of SEQ ID NO: 1; or (b) a DNA having 68% or more (preferably 70% or more, more preferably 75% or more, even more preferably 80% or more, still more preferably 85% or more, further even more preferably 90% or more, further still more preferably 95% or more, further still more preferably 98% or more, and further still more preferably 99% or more) identity to the DNA sequence of SEQ ID NO: 2.

In the method for producing the FADGDH of the present invention described above, the och1 gene of a microorganism belonging to the genus *Aspergillus* may be the following (c) or (d):

(c) a DNA encoding an amino acid sequence having 70% or more (preferably 73% or more, more preferably 74% or more, even more preferably 75% or more, and still more preferably 76% or more) identity to the amino acid sequence of SEQ ID NO: 1; or (d) a DNA having 70% or more (preferably 73% or more, more preferably 74% or more, even more preferably 75% or more, and still more preferably 76% or more) identity to the DNA sequence of SEQ ID NO: 2.

According to a BLAST homology search, the identity to the amino acid sequence of SEQ ID NO: 1 is 70% in the och1 derived from *Aspergillus nidulans,* 73% in the och1 derived from *Aspergillus niger,* 74% in the och1 derived from *Aspergillus kawachii,* 77% in the och1 derived from *Aspergillus terreus,* 78% in the och1 derived from *Aspergillus clavatus*), and 100% in the och1 derived from *Aspergillus flavus.*

In the method for producing the FADGDH of the present invention described above, the sequence of the och1 gene of a microorganism belonging to the genus *Aspergillus* may be the following (e):

(e) a DNA encoding an amino acid sequence having 73% or more (preferably 74% or more, more preferably 76% or more, and even more preferably 99% or more) identity to SEQ ID NO: 2 in a BLAST homology search.

According to a BLAST homology search, the identity to SEQ ID NO: 2 is 74% in the och1 derived from *Aspergillus nidulans,* 76% in the och1 derived from *Aspergillus niger,* 74% in the och1 derived from *Aspergillus clavatus,* and 76% in the och1 gene derived from *Aspergillus terreus.*

The microorganism before modification of the modified microorganism used in the method for producing the FADGDH of the present invention described above is not particularly limited, as long as it has och1 gene. For example, any of the above-listed microorganisms can be used.

The modified microorganism used in the method for producing the FADGDH of the present invention is obtained by reducing the function of the och1 gene of the microorganism before modification. For example, the modified microorganism is selected from a microorganism selected from any one of the following genera: *Aspergillus, Trichoderma, Neurospora, Monascus, Fusarium, Saccharomyces, Pichia, Candida, Schizosaccharomyces, Cryptococcus, Schizophyllum, Mucor, Absidia, Actinomucor, Colletotrichum, Circinella,* and *Arthrinium.*

Among these, microorganisms classified as filamentous fungi, particularly koji molds (microorganisms belonging to the genus *Aspergillus*), secrete and produce large amounts of amylase and glucoamylase, which are sugar-degrading enzymes, and proteases, etc.; thus, they are widely used in the fermentation industry, such as sake, miso, etc. In addition, due to their high protein secretion capacity, they are preferable as expression hosts for producing the FADGDH of the present invention. More preferred among these are *Aspergillus oryzae, Aspergillus niger, Aspergillus terreus,* etc.

The modified microorganism used in the method for producing the FADGDH of the present invention listed above may be a transformant. In this case, a modified microorganism in which the function of the och1 gene is reduced is used as a host microorganism, and FADGDH is produced by using a transformant obtained by introducing a DNA encoding FADGDH into the host microorganism through an appropriate vector. In one embodiment, the FADGDH comprises an N-type sugar chain that consists of a core structure of Man8 GlcNAc2. The N-type sugar chain that consists of the core structure does not have any other mannoses bound to the core structure. In a preferred embodiment, 40% or more, 50% or more, 60% or more, 70% or more, 80 or more, 90% or more, or all of the N-type sugar chains that exist in the FADGDH is the N-type sugar chain that consists of the core structure.

The means for reducing the function of the och1 gene is not particularly limited.

One of the means is to disrupt a DNA corresponding to the och1 gene. This method is suitable when the och1 gene sequence of the microorganism to be used is specified. The term "disrupt" used herein refers to reducing or completely stopping the function of a DNA sequence corresponding to the och1 gene by removing a whole or part of the DNA sequence, adding a mutation to at least one part of the DNA sequence, or inserting any DNA sequence into at least one part, other than the both ends, of the DNA sequence.

The method for producing a modified microorganism in which the function of the och1 gene is reduced may be performed by various known methods, and is not particularly limited.

For example, when a transformant is used, a common method for disrupting the och1 gene uses homologous recombination of DNA. A gene disruption cassette in which an upstream untranslated region and a downstream translated region of a target gene are linked to a marker gene used for transformation is constructed, a host microorganism is transformed to thereby induce homologous recombination in the upstream and downstream of the och1 gene, and the ORF portion of och1 is removed to thereby reduce the function of the gene.

Alternatively, the function of the gene can also be stopped in such a manner that a gene disruption cassette is constructed so that transcription is completed in the inside of ORF of och1, and the gene disruption cassette is inserted in the position of the target gene.

As another means for reducing the function of the och1 gene, it is also possible to obtain a modified microorganism in which the function of the och1 gene is reduced by spontaneous mutation.

In this method, the frequency of spontaneous mutation in a microorganism to be used may be increased by treatment with a mutation agent or by physical treatment, such as irradiation with ultraviolet rays, X-rays, or gamma rays. Naturally occurring variants may also be used.

This method is suitable when, although the function corresponding to the action of the och1 gene is observed in the microorganism to be used, the och1 gene sequence is not specified.

As another means for reducing the expression of the och1 gene, transcription repression by RNA interference (RNAi) can also be used. According to this method, DNA or RNA that serves as a complementary strand of mRNA transcribed by the target gene can be introduced into or transcribed in a microorganism to thereby form a double chain with the mRNA to destabilize the mRNA. Further, translation from mRNA into a peptide can be suppressed to thereby reduce the expression of och1.

This method is effective when it is difficult to disrupt the target gene by targeting in microorganisms with low efficiency for gene homologous recombination.

When the FADGDH of the present invention is produced using a transformant, the genus and/or species in the biological classification of the origin of the FADGDH may be the same or different from the genus and/or species of the host microorganism.

When the FADGDH of the present invention is produced using a transformant, the method for introducing a DNA encoding the FADGDH into a host microorganism and expressing the DNA is not particularly limited. For example, the DNA may be inserted into a suitable vector corresponding to the host, and the vector may be further introduced into the host and transformed. Such a method is standard recombinant DNA technology, and can be performed with reference to, for example, Molecular Cloning, Third Edition, 1.84, Cold Spring Harbor Laboratory Press, New York.

In the method for producing the FADGDH of the present invention, the FADGDH can be produced using a modified microorganism produced by any of the above-mentioned methods. For example, the modified microorganism is cultured and caused to express FADGDH, and the obtained culture medium is purified, thereby producing the FADGDH of the present invention. In general, methods for producing a target protein by purifying a culture medium obtained by culturing a microorganism that expresses the protein have already been established in this technical field.

Therefore, a person skilled in the art can produce FADGDH by applying those findings, and embodiments thereof are not particularly limited.

Examples

The present invention is more specifically described below with reference to Examples; however, the present invention is not limited to the Examples.

1. Selection of och1 Gene Derived from *Aspergillus Oryzae*

Selection of och1 sugar chain synthesis-related genes derived from *Aspergillus oryzae* was performed by selecting sequences with high homology from gene information of yeast *Saccharomyces cerevisiae*, for which sugar chain synthesis-related genes are often studied. SEQ ID NO: 1 represents an amino acid sequence that is assumed to be encoded by the selected gene, and SEQ ID NO: 2 represents a DNA sequence that is assumed to encode och1. The results of homology search in the same genus *Aspergillus* based on information of the amino acid sequence that was assumed to be encoded by the selected gene showed the presence of genes encoding amino acid sequences having 73% identity to *Aspergillus niger*, 77% identity to *Aspergillus fumigatus*, and 70% identity to *Aspergillus nidulans*. This gene cluster is considered to be highly conserved in the genus *Aspergillus*. FIG. 1 shows the results of comparison of the identity of amino acid sequences of och1 orthologs in various *Aspergillus* species.

2. Production of Disruption Cassette of och1 Gene Derived from *Aspergillus Oryzae*

A disruption cassette of the och1 gene of *Aspergillus oryzae* was constructed in the following manner. PCR was performed using genomic DNA of *Aspergillus oryzae* as a template, and using primers represented by SEQ ID NO: 9 and SEQ ID NO: 10 to amplify a region from 2 kbp upstream of the gene to 2 kbp downstream of the gene, containing the och1 gene of *Aspergillus oryzae*. The amplified PCR product was TA-cloned using TArget Clone Plus (produced by Toyobo Co., Ltd.), and inserted into pTA2 vector. The resulting vector was regarded as pTAooch1±2K.

Subsequently, in order to remove the ORF portion of the och1 gene, inverse PCR was performed using the pTAooch1±2K as a template, and using primers represented by SEQ ID NO: 11 and SEQ ID NO: 12. The resulting vector was regarded as pTAooch1±2K-ORF. Then, in order to insert a marker gene, an sC marker portion was cut from pUSA vector using restriction enzyme XbaI and restriction enzyme SbfI, and inserted into the pTAooch1±2K-ORF digested with restriction enzymes NheI and SbfI. The resulting vector was regarded as pTΔAooch1-sC.

3. Production of Sugar Chain Synthesis-Related Gene Disruption Strain

The vector pTΔAooch1-sC obtained in process 2 was mass-produced using the QIAfilter Plasmid Midi Kit (produced by QIAGEN), and used for transformation into koji mold. The recombinant host used was *Aspergillus oryzae* NS4 strain, and the transformation method used was the protoplast-PEG method. FIG. 2 shows the principles of gene disruption. The och1 gene disruption strain was confirmed by PCR and selected from the obtained transformants.

4. Expression of AoFADGDH Gene

FADGDH gene derived from *Aspergillus oryzae* was expressed in the following manner. A region containing niaD was amplified from the genomic DNA of koji mold *Aspergillus oryzae* using a primer of SEQ ID NO: 13 and a primer of SEQ ID NO: 14, and TA-cloned using Target clone plus (produced by Toyobo Co., Ltd.), thereby obtaining pTN. Next, 1 kbp upstream from the translation initiation site of a gene that was assumed as translation elongation factor 1α was amplified by PCR from the genomic DNA of *Aspergillus oryzae* using a primer of SEQ ID NO: 15 and a primer of SEQ ID NO: 16. Further, the AmyB terminator region was amplified by PCR from the genomic DNA of *Aspergillus oryzae* using a primer of SEQ ID NO: 17 and a primer of SEQ ID NO: 18. Regarding the pTN, PCR was performed using a primer of SEQ ID NO: 19 and a primer of SEQ ID NO: 20 to thereby amplify the plasmid. The three PCR products produced as described above were fused using the In-Fusion HD Cloning Kit (Takara Bio, Inc.) to produce expression vector pTNE containing the niaD marker, EF1 promoter, and AmyB terminator.

Subsequently, for FADGDH derived from *Aspergillus oryzae*, the sequence disclosed in International Patent Publication WO2009/119728, that is, a sequence obtained by introducing mutations of G163 R+V 551C into a sequence cloned from cDNA of *Aspergillus oryzae* TI strain, was used. SEQ ID NO: 21 represents an amino acid sequence encoding the FADGDH, and SEQ ID NO: 22 represents a DNA sequence. The FADGDH derived from *Aspergillus oryzae* was amplified using a primer of SEQ ID NO: 23 and a primer of SEQ ID NO: 24. The obtained PCR product was digested with restriction enzyme SpeI, and the gene was inserted, in the forward direction, into the downstream of the EF1 promoter of pTNE similarly digested with SpeI. The resulting vector was regarded as pTNE-AomFADGDH. FIG. 3 shows a vector map of the pTNE-AomFADGDH. The pTNE-AomFADGDH was transformed into Δoch1 strain and NS4 strain. The resulting transformants were cultured in DP medium, and transformants showing the highest productivity were selected.

5. Purification of AomFADGDH

The transformants obtained in process 4 were inoculated in 60 mL of sterilized DP liquid medium placed in a 500-ml Sakaguchi flask, and cultured by shaking at 30° C. for 2 days to prepare a preculture solution. Next, the preculture solution was inoculated in 7.0 L of YPM medium (5% yeast extract, 2% soy peptone, and 5% maltose) placed in a 10-L jar fermenter, and cultured for 3 days under the following conditions: culture temperature=35° C., stirring speed=400 rpm, air flow rate=6.0 L/min, and tube internal pressure=0.2 MPa. Thereafter, the culture solution was filtered through a filter cloth, and the filtrate was collected.

The filtrate was concentrated using a UF membrane (produced by Millipore) having a molecular weight cutoff of 30,000, and a phosphate buffer solution (50 mM, pH of 6.0) was continuously added to the concentrated solution to thereby replace the buffer. Subsequently, 40% (w/v) of ammonium sulfate was gradually added to the concentrated solution. After the mixture was stirred at room temperature for 30 minutes, excess precipitate was removed using a filter aid. Next, the filtrate was charged into 200 mL SP Sepharose Fast Flow (produced by GE HealthCare) column previously equilibrated with 50 mM potassium phosphate buffer solution (pH of 6.0) containing 40% (w/v) of ammonium sulfate, and gradually replaced with 50 mM phosphate buffer solution (pH of 6.0) to elute proteins. Then, the eluted fraction was concentrated using a hollow fiber membrane (produced by Spectrum Laboratories, Inc.) having a molecular weight cutoff of 10,000, and a phosphate buffer solution (50 M, pH of 6.0) was continuously added to the concentrated solution to thereby replace the buffer. Then, DEAE Sepharose Fast Flow (produced by GE Healthcare) column enzyme solution equilibrated with 50 mM phosphate buffer solution (pH of 6.0) was passed, thereby obtaining a purified enzyme. FADGDH expressed in Δoch1 as a host was regarded as Δoch1-AomFADGDH, and FADGDH expressed in the NS4 strain as a host was regarded as AomFADGDH. The resulting AomFADGDH and Δoch1-AomFADGDH were subjected to SDS-PAGE, and molecular weight was observed. For SDS-PAGE, Nu-PAGE 4-12% Bis-Tris Gel (produced by Invitrogen) was used. FIG. 4 shows the results of SDS-PAGE using a molecular weight marker (Bench-Mark™ Protein Ladder) having a molecular weight ladder of 50, 60, 70, 80, 90, 100, 120, 160, and 220 kDa. Further, the shade of the band shown in FIG. 4 was scanned, the molecular weight was plotted on the horizontal axis, and the relative intensity of the band was plotted on the vertical axis, as shown in FIG. 7 (AomFADGDH) and FIG. 8 (Δoch1-AomFADGDH).

The results of SDS-PAGE showed that the molecular weight distribution of AomFADGDH was 80-160 kDa, whereas the molecular weight distribution of Δoch-AomFADGDH was about 70-90 kDa; thus, the range of molecular weight distribution was reduced.

Figure 7:
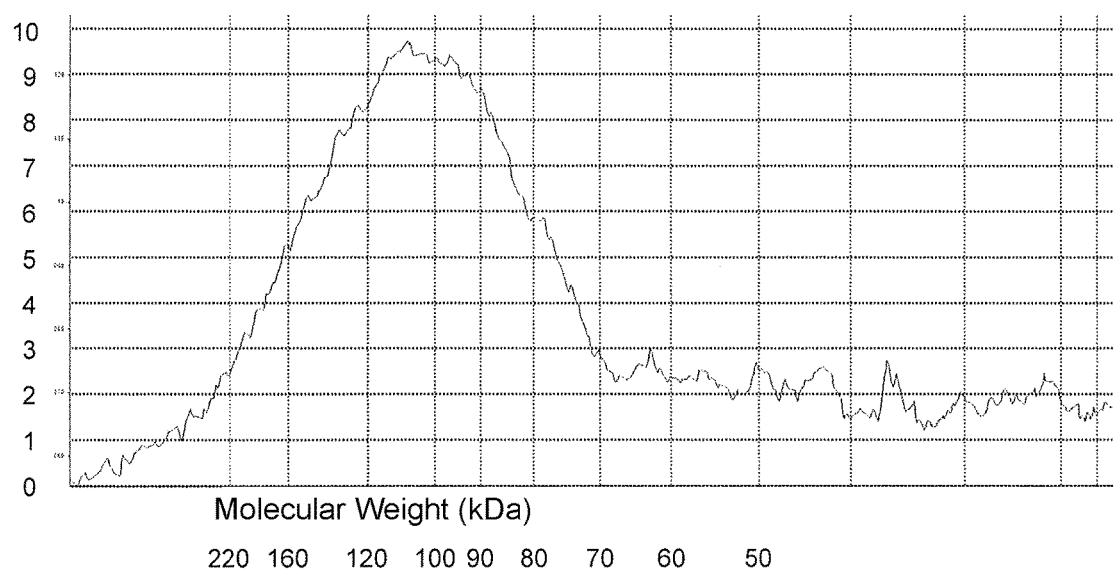
FIG. 7 is a figure obtained by scanning the shade of the band of AomFADGDH shown in FIG. 4, and plotting the molecular weight on the horizontal axis, and the relative intensity of the band on the vertical axis.
Figure 8:
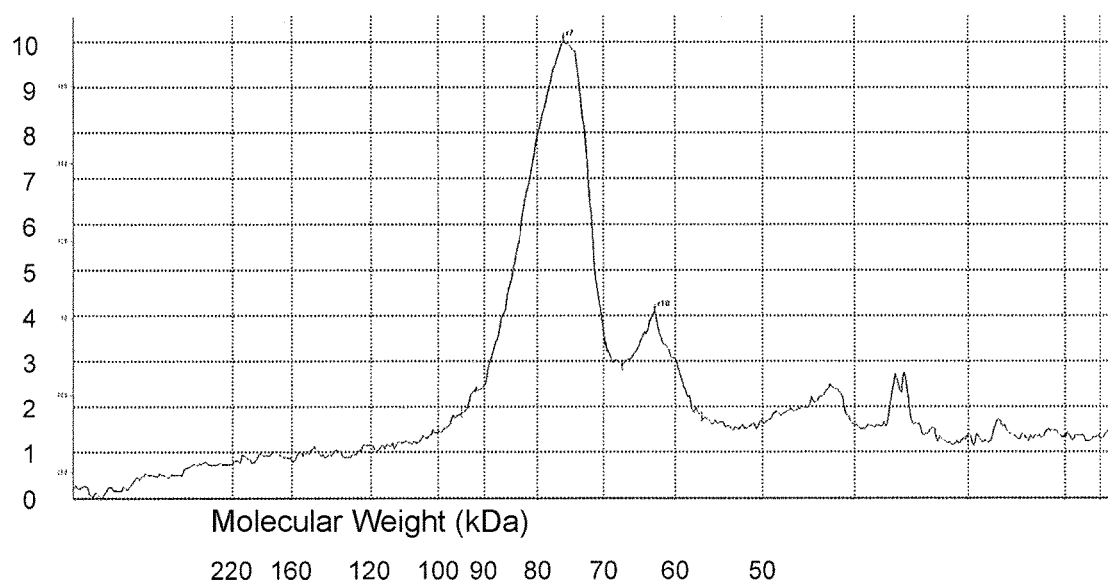
FIG. 8 is a figure obtained by scanning the shade of the band of Δoch1-AOmFADGDH shown in FIG. 4, and plotting the molecular weight on the horizontal axis, and the relative intensity of the band on the vertical axis.

FIG. 7 shows that, in the case of AomFADGDH, the molecular weight with the highest relative intensity of the band resides between 120 kDa and 100 kDa; the molecular weight is determined to be 110 kDa. In contrast, FIG. 8 shows that, in the case of Δoch-AomFADGDH, the molecular weight with the highest relative intensity of the band resides between 80 kDa and 70 kDa; the molecular weight is determined to be 75 kDa.

Thus, the molecular weight of the FADGDH obtained by the production method of the present invention was reduced to 75/110×100=68.2(%), as compared with the wild type. Moreover, since the molecular weight of the polypeptide chain portion alone of the FADGDH was 60 kDa, the sugar chain content was reduced from {(110−60)/110}×100=45.5 (%) of the wild type to {(75−60)/75}×100=20.0(%) (44.0% of the wild type).

The above test results indicate that the range of molecular weight distribution of the FADGDH derived from *Aspergillus oryzae* produced by the production method of the present invention was within 20 kDa when viewed in a molecular weight distribution in which the relative value of band intensity exceeded 60% of the maximum value.

The above test results indicate that the molecular weight of the FADGDH derived from *Aspergillus oryzae* produced by the production method of the present invention was 80% or less (preferably 75% or less, more preferably 70% or less, and even more preferably substantially the same as or less than 68.2%) of that of the wild type.

The above test results indicate that the sugar chain content of the FADGDH derived from *Aspergillus oryzae* produced by the production method of the present invention was 60% or less (preferably 55% or less, and more preferably substantially the same as or less than 44.0%) of that of the wild-type.

The above test results indicate that the molecular weight of the FADGDH derived from *Aspergillus oryzae* produced by the production method of the present invention was 90 kDa or less (preferably 80 kDa or less, and more preferably substantially the same as or less than 75 kDa).

6. Comparison of Influence of Sugar Chain Content on Response Values in Electrochemical Sensor First, a solution of the following formulation (pH=7.0) was produced as a reagent for glucose measurement.

1 mM Sodium citrate (pH of 7.0)
50 mM Potassium ferricyanide
0.4 mg/ml FADGDH

Figure 5:
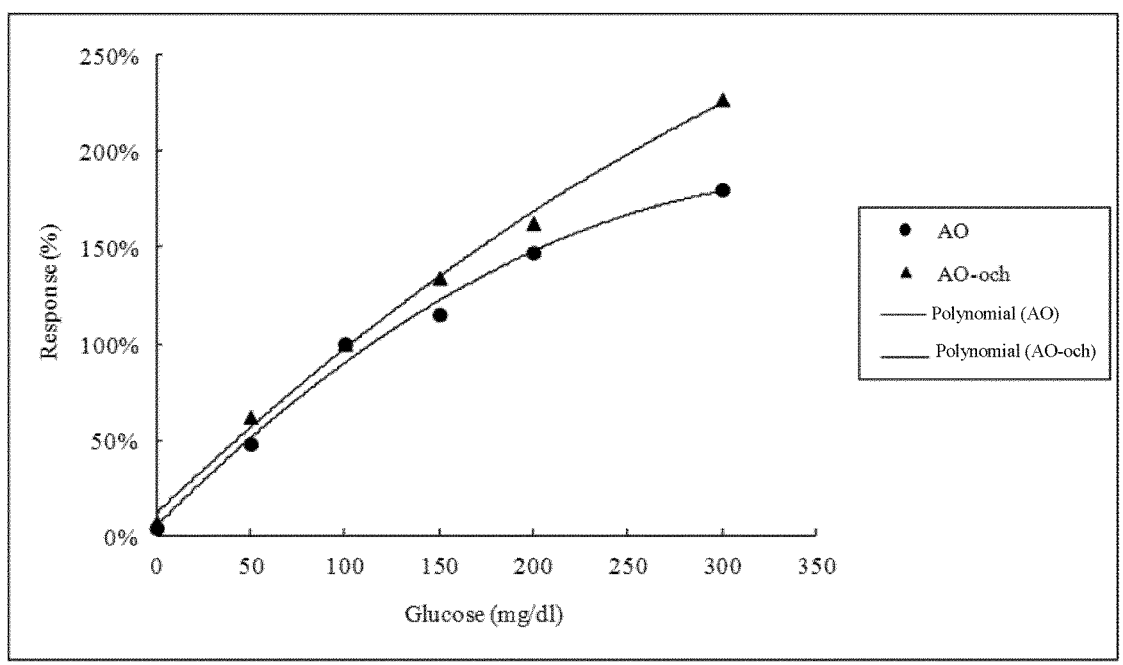
FIG. 5 shows electrode response values measured using purified enzymes AomFADGDH (referred to as "AO" in the figure; plotted by black circles) and Δoch1-AomFADGDH (referred to as "AO-och" in the figure; plotted by black triangles). In the figure, "Polynomial (AO)" and "Polynomial (AO-och)" refer to approximated curves prepared by polynomial approximation of degree 2 based on the plotted measured values.

First, 5 µL of 0.5% CMC (carboxymethylcellulose) was added dropwise on a working electrode, a counter electrode, and a reference electrode of a disposable chip having three electrodes (DEP-CHIP, produced by BioDevice Technology, Ltd.), followed by heating at 50° C. for 10 minutes for drying. Subsequently, 5 µL of the solution of the above formulation was added dropwise to the CMC-fixed portion, followed by heating at 50° C. for 10 minutes, thereby obtaining a sensor chip. The sensor chip was connected to a potentio-galvanostat through a special socket, 5 µL of standard glucose solutions (0 to 300 mg/dl) were added to the composition on the electrode, a voltage of +0.3 V was applied, and current values were monitored. The current value 3 seconds after the voltage was applied was used as a response value. FIG. 5 shows the relationship between the concentration of the glucose standard solutions and the response values.

The measurement results showed that, although the response values of AomFADGDH at from 100 mg/dl to 200 mg/dl were higher than those of Δoch1-AomFADGDH, the response value of AomFADGDH at 300 mg/dl was lower than that of Δoch1-AomFADGDH. It was thus revealed that there was a problem in the response at high concentrations. In contrast, the response values of Δoch1-AomFADGDH linearly increased at up to 300 mg/dl, depending on the concentration of glucose. It was thus revealed that it was advantageous for measurement at high concentrations.

7. Preparation of AtFADGDH

Figure 6:
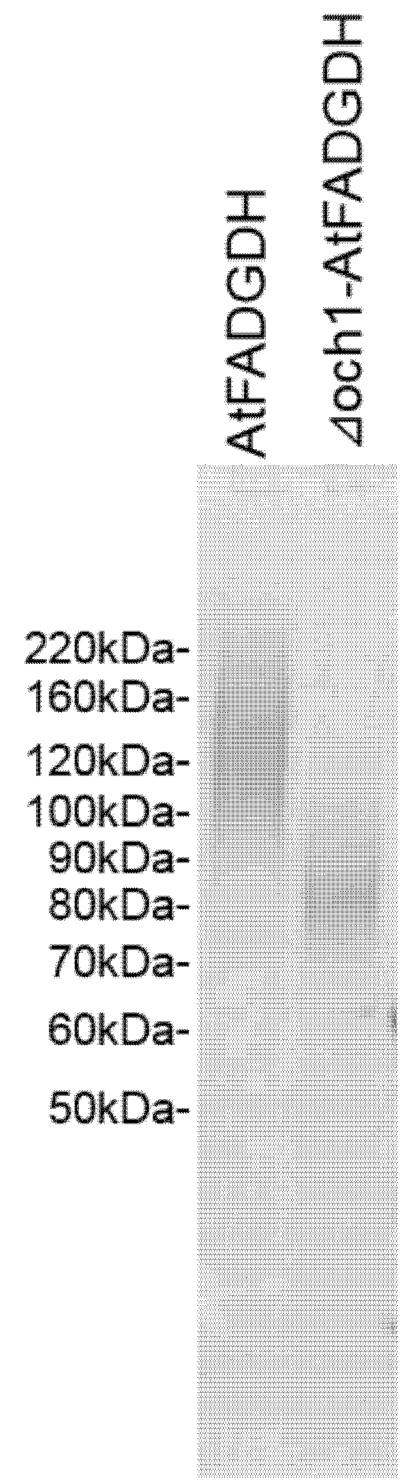
FIG. 6 shows the results of SDS-PAGE of purified enzymes AtFADGDH and Δoch1-AtFADGDH.

Subsequently, in order to confirm the effect of reducing the sugar chain content in FADGDH derived from other microorganisms, FADGDH derived from *Aspergillus terreus* was similarly examined for the effect. The sequence information and characteristics of the FADGDH derived from *Aspergillus terreus* are disclosed in International Patent Publications WO2004/058958 and WO2006/101239. The entire cDNA sequence of the FADGDH derived from *Aspergillus terreus* disclosed in these patent documents was artificially synthesized, and the gene was further inserted into pTNE vector, thereby obtaining pTNE-AtFADGDH. The obtained plasmid was transformed into *Aspergillus oryzae* NS4 strain and Δoch1. From the obtained transformants, transformants showing the highest FADGDH activity were selected, and used to purify FADGDH. Culture and purification of the transformants were performed as described in process 2. FADGDH expressed in Δoch1 as a host was regarded as Δoch1-AtFADGDH, and FADGDH expressed in the NS4 strain as a host was regarded as AtFADGDH. The obtained AtFADGDH and Δoch1-AtFADGDH were subjected to SDS-PAGE, and molecular weight was observed. For SDS-PAGE, Nu-PAGE 4-12% Bis-Tris Gel (produced by Invitrogen) was used. FIG. 6 shows the results of SDS-PAGE using a molecular weight marker (BenchMark™ Protein Ladder). Further, the shade of the band shown in FIG. 6 was scanned, the molecular weight was plotted on the horizontal axis, and the relative intensity of the band was plotted on the vertical axis, as shown in FIG. 9 (AtFADGDH) and FIG. 10 (Δoch1-AtFADGDH).

The results of SDS-PAGE showed that the molecular weight distribution of AtFADGDH was 100-220 kDa, whereas the molecular weight distribution of Δoch-AtFADGDH was about 80-100 kDa; thus, the range of molecular weight distribution was reduced.

Figure 9:
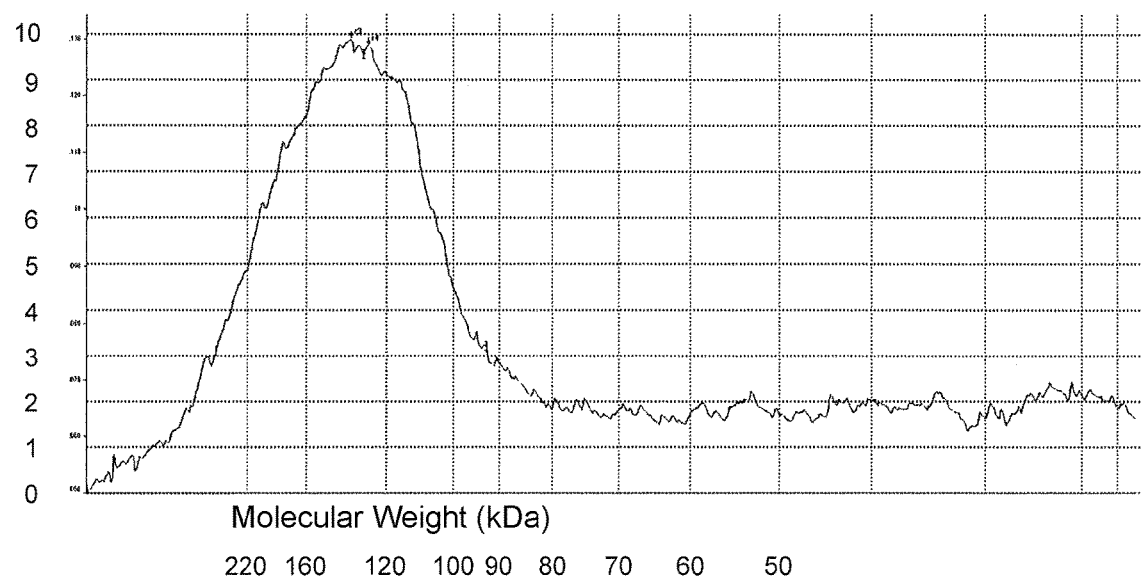
FIG. 9 is a figure obtained by scanning the shade of the band of AtFADGDH shown in FIG. 6, and plotting the molecular weight on the horizontal axis, and the relative intensity of the band on the vertical axis.
Figure 10:
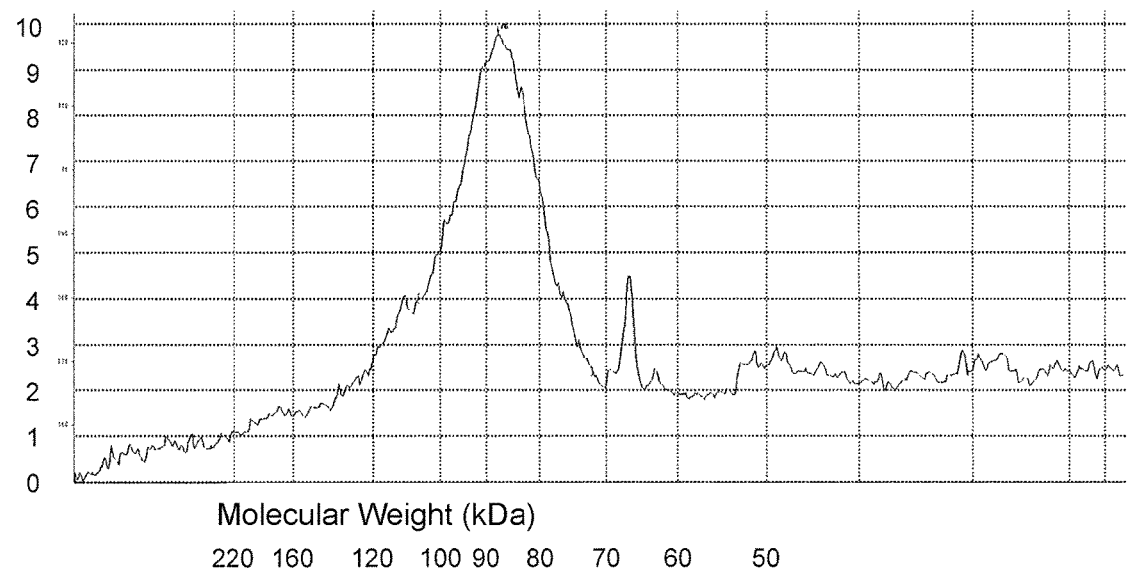
FIG. 10 is a figure obtained by scanning the shade of the band of Δoch1-AtFADGDH shown in FIG. 6, and plotting the molecular weight on the horizontal axis, and the relative intensity of the band on the vertical axis.

FIG. 9 shows that, in the case of AtFADGDH, the molecular weight with the highest relative intensity of the band resides between 160 kDa and 120 kDa; the molecular weight is determined to be 140 kDa. In contrast, FIG. 10 shows that, in the case of Δoch-AtFADGDH, the molecular weight with the highest relative intensity of the band resides between 90 kDa and 80 kDa; the molecular weight is determined to be 85 kDa.

Thus, the molecular weight of the FADGDH obtained by the production method of the present invention was reduced to 85/140×100=60.7(%), as compared with the wild type. Moreover, because the molecular weight of the polypeptide chain portion alone of the FADGDH was 60 kDa, the sugar chain content was reduced from {(140−60)/140}×100=57.1 (%) of the wild type to {(85−60)/85}×100=29.4(%) (51.5% of the wild type).

The above test results indicate that the range of molecular weight distribution of the FADGDH derived from *Aspergillus terreus* produced by the production method of the present invention was within 20 kDa when viewed in a molecular weight distribution in which the relative value of band intensity exceeded 60% of the maximum value.

The above test results indicate that the molecular weight of the FADGDH derived from *Aspergillus terreus* produced by the production method of the present invention was 80% or less (preferably 75% or less, more preferably 70% or less, and even more preferably substantially the same as or less than 60.7%) of that of the wild-type.

The above test results indicate that the sugar chain content of the FADGDH derived from *Aspergillus terreus* produced by the production method of the present invention was 60% or less (preferably 55% or less, and more preferably substantially the same as or less than 51.5%) of that of the wild-type.

The above test results indicate that the molecular weight of the FADGDH derived from *Aspergillus terreus* produced by the production method of the present invention was 90 kDa or less (preferably substantially the same as or less than 85 kDa).

INDUSTRIAL APPLICABILITY

The FADGDH of the present invention is suitable for measuring high-concentration glucose in self-blood glucose measurement, and is very useful for self-blood glucose measurement.

The invention claimed is:

1. A glucose sensor comprising an electrode and a purified FAD-dependent glucose dehydrogenase, wherein the purified FAD-dependent glucose dehydrogenase
   (i) is derived from a microorganism belonging to the genus *Aspergillus* in which the function of the och1 gene is reduced,
   (ii) has a molecular weight from about 75 kDa to about 100 kDa, and
   (iii) comprises a polypeptide having an amino acid sequence with 80% or more identity to the amino acid sequence of SEQ ID NO: 3.

2. A method for measuring glucose concentration comprising applying the glucose sensor according to claim 1 to a sample comprising glucose.

3. The glucose sensor according to claim 1, wherein the polypeptide has the amino acid sequence of SEQ ID NO: 3.

4. A method for measuring glucose concentration comprising applying the glucose sensor according to claim 3 to a sample comprising glucose.

* * * * *